US008299100B2

(12) United States Patent
Silverman et al.

(10) Patent No.: US 8,299,100 B2
(45) Date of Patent: Oct. 30, 2012

(54) POTENT AND SELECTIVE NEURONAL NITRIC OXIDE SYNTHASE INHIBITORS WITH IMPROVED MEMBRANE PERMEABILITY

(75) Inventors: Richard B. Silverman, Northbrook, IL (US); Fengtian Xue, Baton Rouge, LA (US)

(73) Assignee: Northwestern University, Evanston, IL (US)

( * ) Notice: Subject to any disclaimer, the term of this patent is extended or adjusted under 35 U.S.C. 154(b) by 305 days.

(21) Appl. No.: 12/693,196

(22) Filed: Jan. 25, 2010

(65) Prior Publication Data

US 2010/0190230 A1  Jul. 29, 2010

Related U.S. Application Data

(60) Provisional application No. 61/205,770, filed on Jan. 23, 2009.

(51) Int. Cl.
*A61K 31/4439*  (2006.01)
*C07D 401/06*  (2006.01)

(52) U.S. Cl. .................. 514/343; 546/278.4
(58) Field of Classification Search .............. 514/343; 546/278.4
See application file for complete search history.

(56) References Cited

U.S. PATENT DOCUMENTS

| 7,470,790 | B2 | 12/2008 | Silverman |
| 2005/0107369 | A1 | 5/2005 | Silverman et al. |
| 2008/0108814 | A1 | 5/2008 | Silverman |
| 2008/0176907 | A1 | 7/2008 | Silverman et al. |

OTHER PUBLICATIONS

Xue et al. Bioorganic & Medicinal Chemistry Letters 2010, 20, 554-557, which was available online Nov. 22, 2009.*
Ji, Hairao et al. Discovery of Highly Potent and Selective Inhibitors or Neuronal Nitric Oxide Synthase by Fragment Hopping. J. Med. Chem. 2009 (Published on Web Jan. 6, 2009), vol. 52, pp. 779-797.
Bertrand Le Bourdonec et al. Discovery of a Series of Aminopiperidines as Novem iNOS Inhibitors. Bioorganic & Medicinal Chemistry Letters, 2008, vol. 18, pp. 336-343.
Hah, Jung-Mi et al. Aromatic Reduced Amide Bond Peptidomimetics as Selective Inhibitors of Neuronal Nitric Oxide Synthase. J. Med. Chem. 2003, vol. 46, pp. 1661-1669.
Jones, T.A.; Zou, J.-Y.; Cowan, S.W. "Improved Methods for Building Protein Models in Electron Density Maps and the Location of Errors in these Models." Acta Cryst. (1991), A47, 110-119.
Winn, M.D.; Isupov, M.N.; Murshudov, G.N. "Use of TLS Parameters to Model Anisotropic Displacements in Macromolecular Refinement." Acta Cryst. (2001), D57, 122-133.
Emsley, P.; Cowtan, K. "Coot: Model-Building Tools for Molecular Graphics." Acta Cryst. (2004), D60, 2126-2132.
Murshudov, G.N.; Vagin, A.A.; Dodson, E.J. "Refinement of Macromolecular Structures by the Maximum-Likelihood Method." Acta Cryst. (1997), D53, 240-255.
Li, H.; Shimizu, H.; Flinspach, M.; Jamal, J.; Yang, W.; Xian, M.; Cai, T.; Wen, E.Z.; Jia, Q.; Wang, P.G.; Poulos, T.L. "The Novel Binding Mode of N-Alkyl-N'-hydroxyguanidine to Neuronal Nitric Oxide Synthase Provides Mechanistic Insights into NO Biosynthesis." Biochemistry 2002, 41, 13868-13875.
Tchilibon, S.; Kim, S-K; Gao, Z-G; Harris, B.A.; Blaustein, J.B.; Gross, A.S.; Duong, H.T.; Melman, N.; Jacobson, K.A. "Exploring Distal Regions of the A3 Adenosine Receptor Binding Site: Sterically Constrained N6-(2-phenylethyl) Adenosine Derivatives as Potent Ligands." Bioorganic & Medicinal Chemistry 12 (2004), 2021-2034.
Pryde, D.C.; Cook, A.S.; Burring, D.J.; Jones, L.H.; Foll, S.; Platts, M.Y.; Sanderson, V.; Corless, M.; Stobie, A.; Middleton, D.S.; Foster, L.; Barker, L.; Van Der Graaf, P.; Stacey, P.; Kohl, C.; Coggon, S.; Beaumont, K. "Novel Selective Inhibitors of Neutral Endopeptidase for the Treatment of Female Sexual Arousal Disorder." Bioorganic & Medicinal Chemistry 15 (2007), 142-159.
Lakshmipathi, P.; Crevisy, C.; Gree, R. "Reaction Monitoring in LPOS by 19F NMR. Study of Soluble Polymer Supports with Fluorine in Spacer or Linker Components of Supports." J. Comb. Chem. 2002, 4, 612-621.
Rosen, T.C.; Yoshida, S.; Frohlich, R.; Kirk, K.L.; Haufe, G. "Fluorinated Phenylcyclopropylamines. 2. Effects of Aromatic Ring Substitution and of Absolute Configuration on Inhibition of Microbial Tyramine Oxidase." J. Med. Chem. 2004, 47, 5860-5871.
McPhillips, T.M.; McPhillips, S.E.; Chiu, H-J; Cohen, A.E.; Deacon, A.M.; Ellis, P.J.; Garman, E.; Gonzalez, A.; Sauter, N.K.; Phizackerley, R.P.; Soltis, S.M.; Kuhn, P. "Blu-Ice and the Distributed Control System: Software for Data Acquisition and Instrument Control at Macromolecular Crystallography Beamlines." J. Synchrotron Rad. (2002), 9, 401-406.
Hevel, J.M.; Marletta, M.A. "Nitric-Oxide Synthase Assays." Methods in Enzymology, vol. 233 (1994), 250-258.
Flinspach, M.L.; Li, H.; Jamal, J.; Yang, W.; Huang, H.; Hah, J-M; Gomez-Vidal, J.A.; Litzinger, E.A.; Silverman, R.B.; Poulos, T.L. "Structural Basis for Dipeptide Amide Isoform-Selective Inhibition of Neuronal Nitric Oxide Synthase." Nature Structural & Molecular Biology, vol. 11, No. 1, (Jan. 2004), 54-59.

\* cited by examiner

*Primary Examiner* — Joseph Kosack
*Assistant Examiner* — Matthew Coughlin
(74) *Attorney, Agent, or Firm* — Reinhart Boerner Van Deuren s.c.

(57) ABSTRACT

Compounds and related compositions and methods as can be used to inhibit neuronal nitric oxide synthase and can be employed in the treatment of various neurodegenerative diseases, such compounds of a formula

22 Claims, 4 Drawing Sheets

Figure 3A
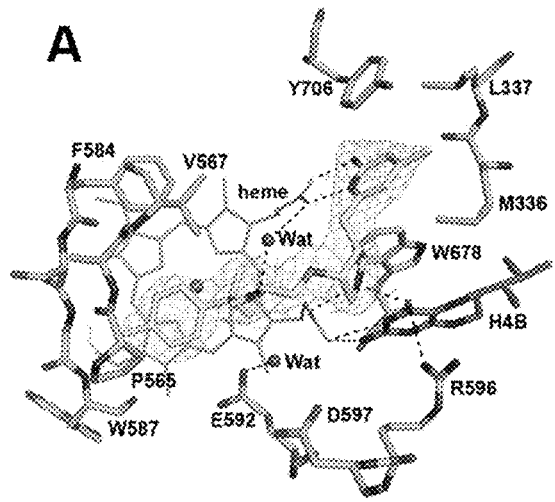
Figure 3B
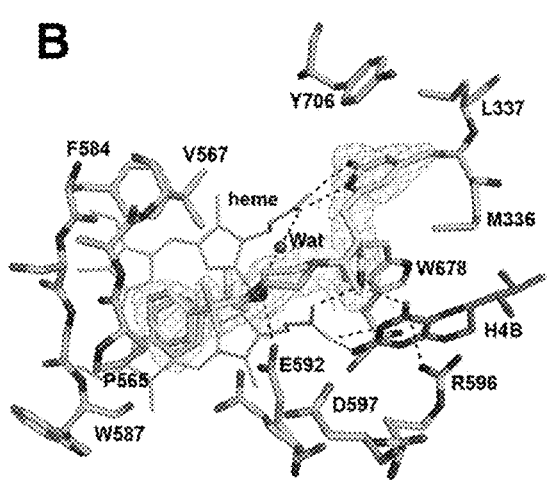
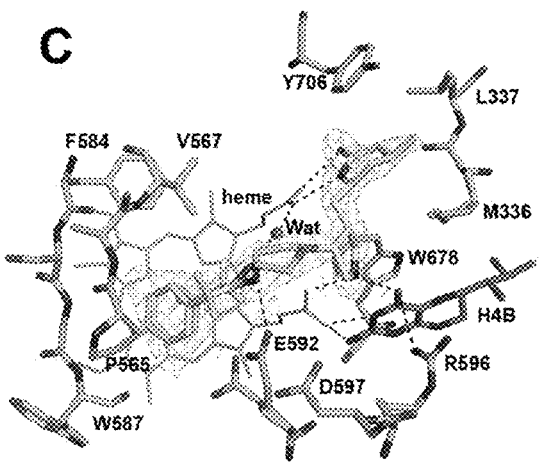
Figure 3C
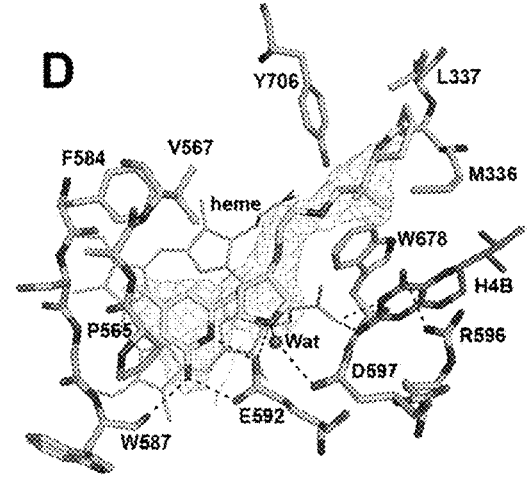
Figure 3D

POTENT AND SELECTIVE NEURONAL NITRIC OXIDE SYNTHASE INHIBITORS WITH IMPROVED MEMBRANE PERMEABILITY

This application claims priority benefit from application Ser. No. 61/205,770 filed Jan. 23, 2009, the entirety of which is incorporated herein by reference.

This invention was made with government support under Grant No. R01 GM49725 awarded by the National Institutes of Health to Northwestern University. The government has certain rights in the invention.

BACKGROUND OF THE INVENTION

Neuronal nitric oxide synthase (nNOS) catalyzes the oxidation of L-arginine to L-citrulline in the central nervous system, generating nitric oxide (NO), a critical neurotransmitter. Significant research has implicated the overexpression of nNOS—and overproduction of NO—in various neurological diseases, including Parkinson's, Alzheimer's, and Huntington's diseases, as well as neuronal damage due to stroke Inhibiting endothelial nitric oxide synthase (eNOS) and inducible nitric oxide synthase (iNOS) is, however, undesirable, because these isozymes are responsible for maintaining crucial body function. Thus, selective inhibition of nNOS over its closely related isoforms, eNOS and iNOS, can provide a promising strategy in developing therapeutics for the treatment of neurodegenerative diseases.

Through on-going research of nNOS selective inhibitors, a pyrrolidine-based compound (1, FIG. 1), was found to provide great potency ($K_i$=15 nM) and very high selectivity for nNOS over eNOS (2100 fold) and iNOS (630 fold). However, despite the promising inhibitory activity of 1, further application to neurodegenerative therapeutics has been impeded by several structural characteristics. First, the flexible m-fluorophenyl ethanamino tail brought multiple rotatable bonds to the inhibitor, limits the potency and selectivity of 1. In addition, the benzylic position of the m-fluorophenyl ring is highly susceptible to metabolic oxidation reactions. More importantly, the two positive charges of 1 at physiological pH, derived from the two amino groups, decreases the chance of 1 to penetrate the blood brain barrier (BBB).

SUMMARY OF THE INVENTION

In light of the foregoing, it is an object of the present invention to provide compounds, compositions and related methods of use for the selective inhibition of neuronal nitric oxide synthase, thereby overcoming various deficiencies and shortcomings of the prior art including those outlined above. It would be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide one or more small molecule and/or non-peptide compounds exhibiting selective nNOS inhibition over other enzyme isoforms and providing improved membrane permeability and bioavailability.

It can be another object of the present invention to provide an enantiomerically-pure compound to affect binding orientation and improved potency and selectivity over the corresponding racemic mixtures.

It can be another object of the present invention, alone or in conjunction with one or more of the preceding objectives, to reduce basicity of an ethanamino nitrogen center, as can be accomplished by incorporation of an electron-withdrawing moiety adjacent or proximate thereto, to reduce molecular cationic character at physiological pH and to enhance bioavailability by improved penetration of the BBB.

It can be another object of the present invention to provide one or more such non-peptide compounds for in vitro use and study under conditions promoting nitric oxide production, indicative of one or more mammalian disease states.

Alternatively, it can also be an object of the present invention to provide one or more such compounds enabling in vivo treatment of such disease states.

Other objects, features, benefits and advantages of the present invention will be apparent from this summary and the following descriptions of certain embodiments of such compounds, compositions and/or methods and will be readily apparent to those skilled in the art having knowledge of the synthetic techniques described herein. Such objectives, features, benefits and advantages will be apparent from the above as taken into conjunction with the accompanying examples, data, figures and references incorporated herein, together with all reasonable inferences to be drawn therefrom.

Accordingly, in part, the present invention can relate to compounds of a formula

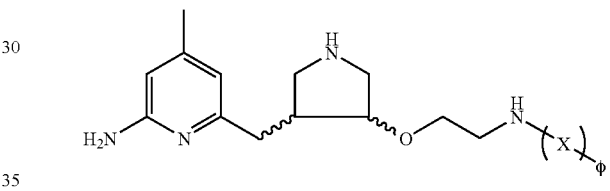

wherein X can be selected from divalent electron-withdrawing moieties or groups and/or substituents thereof, together with salts, hydrates and/or solvates of such compounds; and to pharmaceutical compositions comprising one or more such compounds, optionally together with an acceptable carrier component. In certain embodiments, without limitation, such moieties/groups can be selected from ether, cyclopropyl, monofluoroethylene and difluoroethylene, such groups/moieties as are illustrated below and discussed more fully elsewhere herein. More generally, such groups/moieties and substituents thereof are limited only by electron-withdrawing function, as can be considered in the context of mitigation or partial removal of a degree of positive charge from an amine functionality, such as at physiological pH. Accordingly, without limitation, in certain such embodiments, such a compound can be present as an acid salt, either partially or fully protonated. In certain such embodiments, the counter ion(s) can be a conjugate base of a protic acid. Regardless, Φ can be selected from moieties capable of contribution to or affect on enzyme binding or interaction. Without limitation, Φ can be as discussed below.

More generally, as demonstrated below, the structure of such a compound is limited only by choice of starting material or reagent, enroute to a pyridine substructure (I), pyrrolidine substructure (II) and/or lipophilic tail substructure (III), such substructures as are discussed more fully below and/or in co-pending application Ser. No. 11/906,283 and U.S. Pat. No. 7,470,790, each of which is incorporated herein by reference in its entirety. Accordingly, various compounds of this invention can, optionally, comprise various other substructures I, II and/or III or other moieties and/or substituents thereof, such as the substructures, moieties and/or groups described in the aforementioned incorporated references. As such, with respect to the broader aspects of this invention, the present compounds are without stereochemical limitation. Where such compounds and/or their intermediates are available as racemic mixtures, the respective isomers can be resolved. Likewise, as such compounds are diastereomers, the corresponding enantiomers can be separated. Accordingly, any such stereocenter can be (S) or (R) with respect to any other stereocenter(s), whether such a compound is present as a salt, hydrate and/or solvate thereof.

In part, the present invention can also provide a method of inhibiting a nitric oxide synthase, such a method comprising contacting a nitric oxide synthase with an effective amount of any one or more of the present compounds, including, but not limited to those illustrated by the following examples, referenced figures and/or accompanying synthetic schemes. More specifically, as also supported herein, the present invention can provide a method of using an electron withdrawing moiety to inhibit such a nitric oxide synthase and/or for selective inhibition of neuronal nitric oxide synthase. Such a method can comprise providing a compound or a related composition of this invention; and contacting a nitric oxide synthase enzyme with such a compound/composition, such contact as can selectively inhibit neuronal nitric oxide synthase over inducible and/or endothelial isoforms.

BRIEF DESCRIPTION OF THE DRAWINGS

FIGS. 2, 3, and 4 were prepared with PyMol, an open-source, user-sponsored molecular visualization system well-known to those skilled in the art.

FIGS. 3A-D The nNOS active site with 2dc (A), 2dd (B), 2e (C), or 2f (D) bound. Around each inhibitor is the sigmaA weighted 2Fo–Fc density contoured at 1 σ. Major hydrogen bonds are depicted with dashed lines. Note the alternate conformations for E592 occur when the inhibitor shows multiple conformations in the nNOS-2dd or nNOS-2e structure.

DETAILED DESCRIPTION OF CERTAIN EMBODIMENTS

Figure 1:
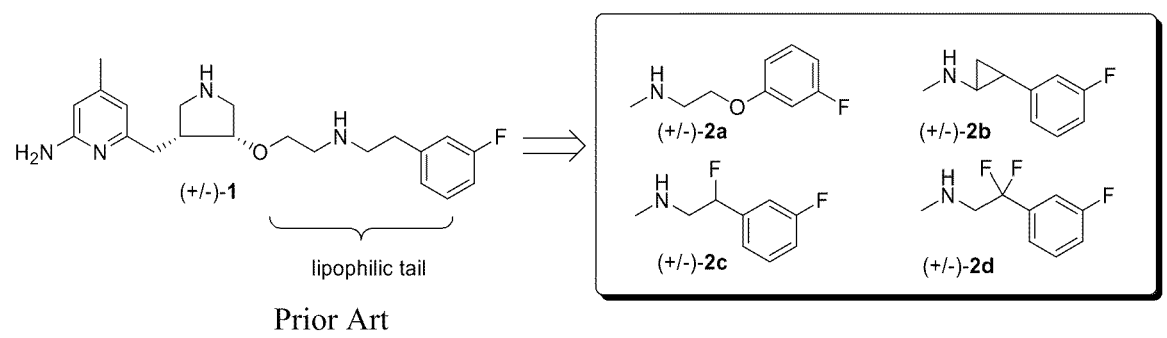
FIG. 1 shows development and design of several non-limiting compounds of this invention from prior art compound 1.

To address permeability problems of the sort discussed above, different strategies have been applied to improve the bioavailability of the prior art compounds—including, without limitation, the design, synthesis, and biological evaluation of a new series of low $pK_a$ inhibitors (e.g., compounds 2a-d of FIG. 1). In representative such embodiments, different electron withdrawing groups, including ether (2a), cyclopropyl (2b), monofluoromethylene (2c), and difluoromethylene (2d), were introduced at the position adjacent or proximate to the pendent amine group in the lipophilic tail of 1 (FIG. 1). While the chemical structures of these inhibitors are related to that of 1, the predicted $pK_a$ values of these compounds are significantly and unexpectedly lower than 1 (Table 1): supporting the hypothesis was that an additional electron withdrawing group, which can be considered to mitigate or partially remove the positive charge from the amine functionality through electronegative induction, would decrease cationic character of inhibitors 2a-d compared to 1, and therefore, improve membrane permeability of the inhibitors.

TABLE 1

Physiochemical properties of inhibitors 1 and 2a-d.

| Compound | $M_w$ | $pK_a{}^a$ |
|---|---|---|
| 1 | 372 | 8.94 |
| 2a | 388 | 8.12 |
| 2b | 384 | 7.37[b] |
| 2c | 390 | 7.32 |
| 2d | 408 | 5.56 |

[a]Lipophilicity data were calculated with ACD/LogD version 7.0, Advanced Chemistry Development, Inc., Toronto, Canada.
[b]These data were calculated based on a previous report. (Perrin, C. L.; Fabian, M. A.; Rivero, I. A. Basicities of cycloalkylamines: Baeyer strain theory revisited. Tetrahedron 1999, 55, 5773-5780.)

Illustrating various such embodiments of this invention, a series of nNOS inhibitors (2) provides a structurally constrained cyclopropyl ring inserted in the position adjacent to the amine group of the ethanamino tail. The introduction of the cyclopropyl group of the new inhibitors (2) can potentially enhance the inhibitory activity by stabilizing a biologically active conformer (therefore reducing the energetic penalty on binding to the enzyme), and improve selectivity by eliminating bioactive conformers that give undesired biological responses. In addition, the insertion of a cyclopropyl fragment can block the potential metabolic oxidation at the benzylic position of the m-fluorophenyl ring. Furthermore, the electro-withdrawing character of the cyclopropyl ring decreases the basicity of the adjacent amino group. The calculated pKa value of the amino group in the lipophilic tail of such embodiments of inhibitor 2 was ~7.4, which was significantly lower than that of 1. As a result, pseudo-monocationic cyclopropyl variations of inhibitor 2 should have improved BBB permeability.

Generally, a representative synthesis of 4b is detailed in Scheme 1a, below. Acid-catalyzed esterification of carboxylic acid 5 provided methyl ester 6, which was treated with diazomethane ($CH_2N_2$) in the presence of a catalytic amount of $Pd(OAc)_2$ to generate cyclopropyl methyl ester 7 in excellent yields. Saponification of 7 in aqueous NaOH (2N) gave carboxylic acid 8, which was converted to a Boc-protected amine 9 through a Curtius rearrangement. (Tchilibon, S.; Kim, S.-K.; Gao, Z.-G.; Harris, B. A.; Blaustein, J. B.; Gross, A. S.; Duong, H. T.; Melman, N.; Jacobson, K. A. Exploring distal regions of the A3 adenosine receptor binding site: sterically constrained N6-(2-phenylethyl)adenosine derivatives as potent ligands. *Bioorg. Med. Chem.* 2004, 12, 2021-2034.) Finally, the Boc-protecting group of 9 was removed with TFA to provide 4b as a TFA salt in high yields.

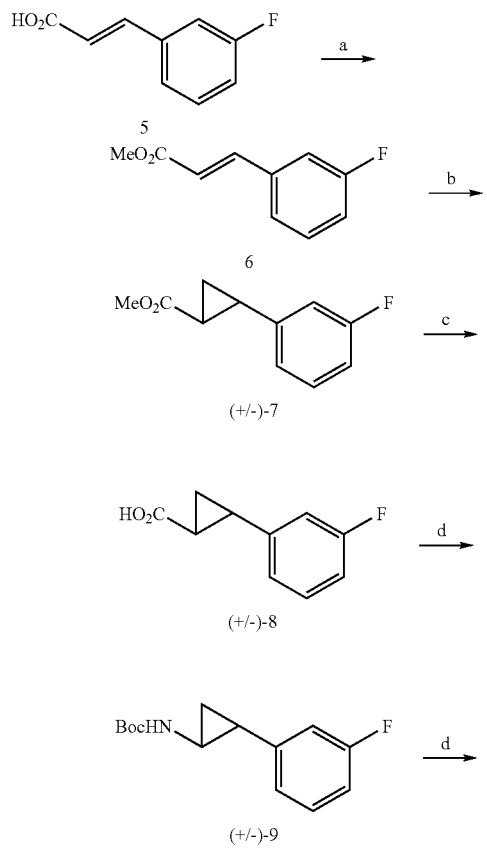

Scheme 1a. Synthesis of 2-(3-Fluorophenyl)cyclopropanamine 4b[a]

[a]Reagents and conditions: (a) H$_2$SO$_4$, MeOH, reflux, 24 h, 99%;
(b) CH$_2$N$_2$, Pd(OAc)$_2$, ether/CH$_2$Cl$_2$, 0° C. - r.t., 2 h, 100%; (c) NaOH
(2 N), MeOH, r.t., 2 h, 99%; (d) DPPA, Et$_3$N, t-BuOH, 85° C., 48 h, 82%;
(e) TFA/CH$_2$Cl$_2$ (1:2), r.t., 45 min, 100%.

Alternatively, illustrating another synthetic route, consider the preparation of 3a-c shown in Scheme 1b. (As a departure from the aforementioned general numbering format, the following compounds 4-9 are illustrated in Schemes 1b-e (and described in examples 5-29) en route to several non-limiting representative variations of inhibitor compound 2b: for instance, cyclopropyl inhibitors 2ba-2bd, in Scheme 1d, below). Rhodium (II)-catalyzed cyclopropanation of 1-substituted-3-vinylbenzene (4a-c) provided 5a-c as a cis/trans mixture in good yields. Next, ethyl ester 5a-c were treated with NaOMe in refluxing EtOH to induce the epimerization reaction, generating the thermodynamically more stable trans isomers, which were hydrolyzed in aqueous LiOH to provide 6a-c in good yields. (See, Pryde, D. C.; Cook, A. S.; Burring, D. J.; Jones, L. H.; Foll, S.; Platts, M. Y.; Sanderson, V.; Corless, M.; Stobie, A.; Middleton, D. S.; Foster, L.; Barker, L.; Graaf, P. V. D.; Stacey, P.; Kohl, C.; Coggon, S.; Beaumont, K. "Novel Selective Inhibitors of Neutral Endopeptidase for the Treatment of Female Sexual Arousal Disorder." *Bioor. Med. Chem.* 2007, 15, 142.) Carboxylic acids 6a-c were converted to Boc-protected amines (7a-c) through Curtius rearrangement reactions in reasonable yields. (See, Tchilibon, S., et al., supra.) Finally, the Boc-protecting groups of 7a-c were removed in trifluoroacetic acid (TFA) to provide 3a-c as TFA salts in high yields.

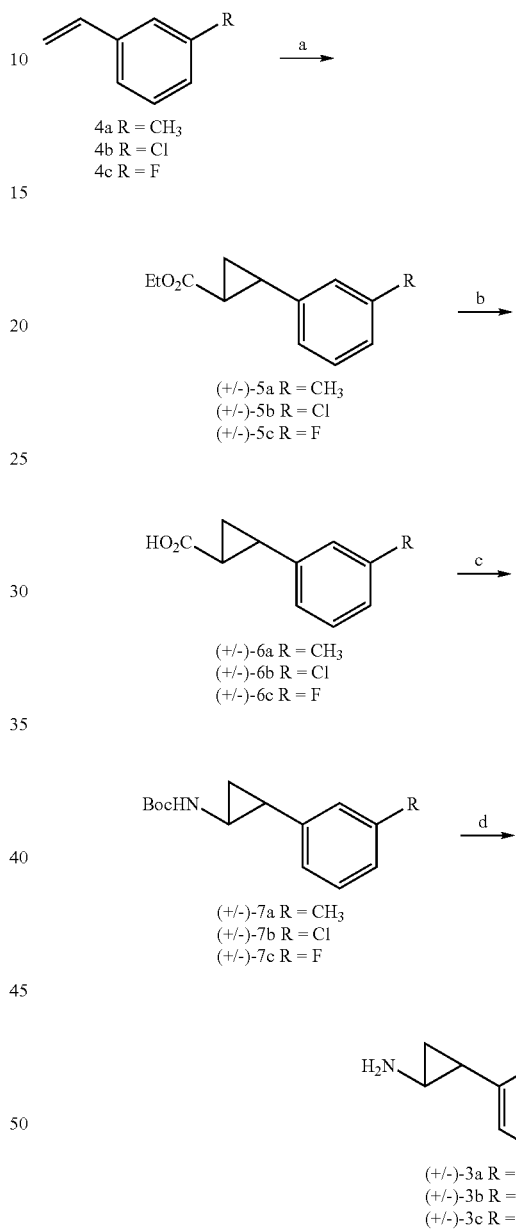

Scheme 1b. Synthesis of 3a-c[a]

[a]Reagents and conditions: (a) EtO$_2$CCHN$_2$, Rh$_2$(OAc)$_4$, toluene, 80-85° C.,
2 h; (b) (i) NaOMe in EtOH (1M), reflux, 40 h, (ii) LiOH, MeOH/H$_2$O,
70° C., 16 h, 75-80% for two steps; (c) DPPA, triethylamine, t-BuOH,
85° C., 48 h, 75-82%; (d) TFA/CH$_2$Cl$_2$ (1:2), r.t., 45 min.

The two enantiomers of 3c were resolved through their camphanic amides (Scheme 1c). First the racemic mixture of 3c was treated with (S)-(−) camphanic chloride in the presence of triethylamine (TEA) to generate two separable diastereomers 8a and 8b in high yields. Next, the amide bonds of 8a and 8b were hydrolyzed in concentrated HCl to provide single enantiomers 3d and 3e in good yields.

Scheme 1c. Resolution of enantiomers 3d and 3e[a]

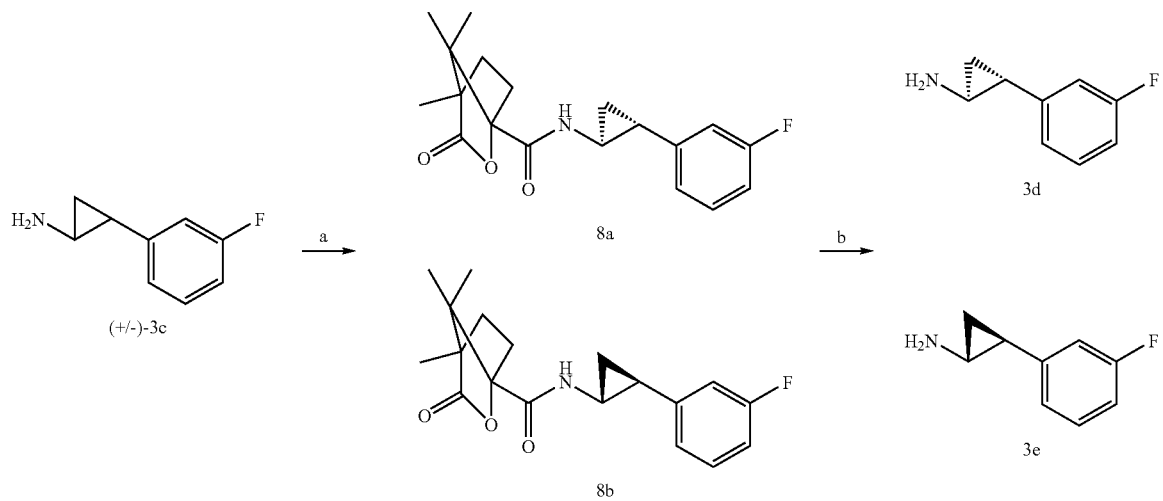

[a]Reagents and conditions: (a) (S)-(-)-comphanic chloride, DCM, TEA, r.t., 30 min, 81% for two diastereomers in total; (b) 12N HCl, EtOH (2:1), reflux, 72 h, 67-70%.

As illustrated in Scheme 1d, reductive amination of aldehyde 8 with amines 3a-d using NaHB(OAc)$_3$ as a reducing reagent gave 9a-d in high yields. Next, the three Boc-protecting groups of 9a-d were removed in HCl to yield the final inhibitors (2ba-bd) in excellent yields.

Scheme 1d. Synthesis of 2ba-bd.[a]

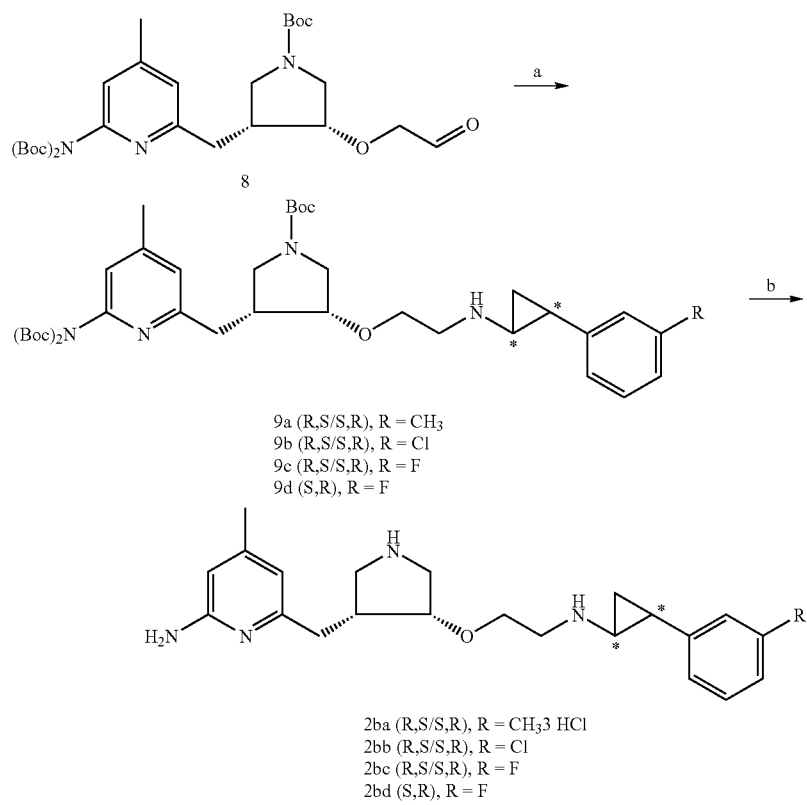

9a (R,S/S,R), R = CH$_3$
9b (R,S/S,R), R = Cl
9c (R,S/S,R), R = F
9d (S,R), R = F

2ba (R,S/S,R), R = CH$_3$ 3 HCl
2bb (R,S/S,R), R = Cl
2bc (R,S/S,R), R = F
2bd (S,R), R = F

[a]Reagents and conditions: (a) amine hydrochloride, TEA, NaHB(OAc)$_3$, rt, 3 h, 81-87%; (d) 6N HCl in MeOH (2:1), rt, 16 h, 90-99%.

For purpose of comparison and to demonstrate the relative effectiveness of inhibitors 2a-d, compound 10 was synthesized as shown in Scheme 1e. Reductive amination of aldehyde 11 with amine 3e provided the corresponding secondary amine, which was then protected by a Boc-protecting group to give 12 in reasonable yields. Catalytic hydrogenation of 12 using Pd(OH)$_2$/C as a catalyst at 60° C. removed the Bn-protecting group. At the same time, the cyclopropyl group was reduced to generate compound 13 as a single enantiomer. Finally, the three Boc-protecting groups were removed in HCl to provide inhibitor 10 as an HCl salt in good yields.

Scheme 1e. Synthesis of inhibitors 10[a]

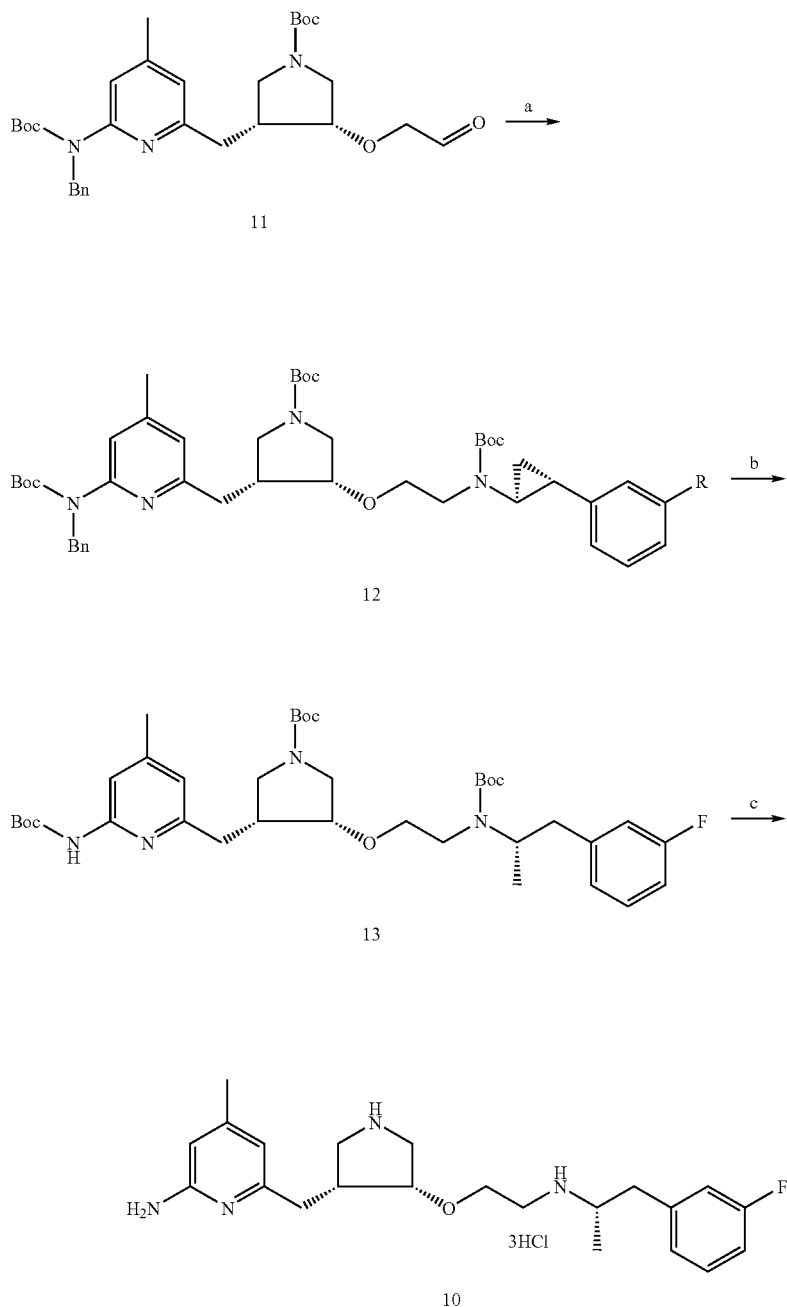

[a] Reagents and conditions: (a) (i) 3e, TEA, NaHB(OAc)$_3$, r.t., 3 h, (ii) (Boc)$_2$O, TEA, MeOH, r.t., 6 h, 60% for two steps; (b) H$_2$, Pd(OH)$_2$/C, 60° C., 30 h; (c) 6N HCl/MeOH (2:1), r.t., 16 h, 25% for two steps.

As shown in Scheme 2, the synthesis of 4c began with 3-fluorostyrene 10. Bromofluorination of 10 using NBS and Et$_3$N.3HF generated 1-(2-bromo-1-fluoroethyl)-3-fluorobenzene 11 in a high yield. (See, Rosen, T. C.; Yoshida, S.; Fröhlich, R.; Kirk, K. L.; Haufe, G. Fluorinated phenylcyclopropylamines. 2. Effects of aromatic ring substitution and of absolute configuration on inhibition of microbial tyramine oxidase. *J. Med. Chem.* 2004, 47, 5860-5871.) Next, 11 was converted to azide (12) using NaN$_3$ in DMSO at 65° C. in a good yield. (Other solvents such as THF and DMF did not give satisfactory yields.) Finally, catalytic hydrogenation of 12 in a mixture of EtOH and 1 N HCl (2:1) provided 4c as a HCl salt in an excellent yield.

Crévisy, C.; Grée, R. Reaction monitoring in LPOS by $^{19}$F NMR. Study of soluble polymer supports with fluorine in spacer or linker components of supports. *J. Comb. Chem.* 2002, 4, 612-621.) Next, 14 was allowed to react with NaN$_3$ in DMSO at 110° C. to give azide (15) in a good yield. Finally, 15 was subjected to catalytic hydrogenation under acidic conditions to give 4d as an HCl salt in a good yield.

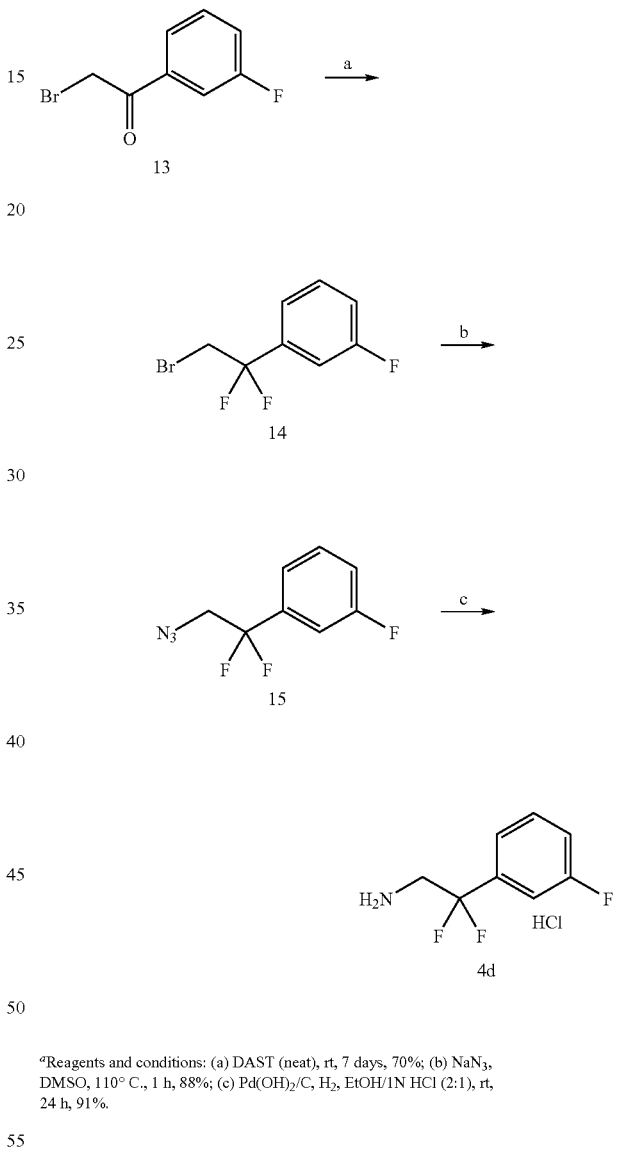

$^a$Reagents and conditions: (a) NBS, Et$_3$N•3HF, CH$_2$Cl$_2$, 0° C. to r.t., 12 h, 85%; (b) NaN$_3$, DMSO, 65° C., 4 h, 85%; (c) Pd(OH)$_2$/C, H$_2$, EtOH/1N HCl (2:1), r.t., 24 h, 98%.

$^a$Reagents and conditions: (a) DAST (neat), rt, 7 days, 70%; (b) NaN$_3$, DMSO, 110° C., 1 h, 88%; (c) Pd(OH)$_2$/C, H$_2$, EtOH/1N HCl (2:1), rt, 24 h, 91%.

Generally, a representative synthesis of a difluoroethanamine is as shown in Scheme 3. 2-Bromo-3'-fluoroacetophenone 13 was treated with diethylaminosulfur trifluoride (DAST) to give 1-(2-bromo-1,1-difluoroethyl)-3-fluorobenzene 14 in good yield. (See, Lakshmipathi, P.;

With 4a-d in hand, the syntheses of inhibitors 2a-d were completed using a three-step procedure (Scheme 4). First, reductive amination between 3 and 4a-d using NaHB(OAc)$_3$ gave 16a-d in modest yields. To simplify the purification process, the resulting secondary amines (16a-d) were protected with (Boc)$_2$O to give 17a-d. Finally, the Bn-protecting group and the three Boc-protecting groups were removed at the same time in a mixture of EtOH and 12 N HCl (2:1) under high pressure catalytic hydrogenation conditions to provide 2a-d as HCl salts in good yields.

Scheme 4. Synthesis of Inhibitors 2a-d[a]

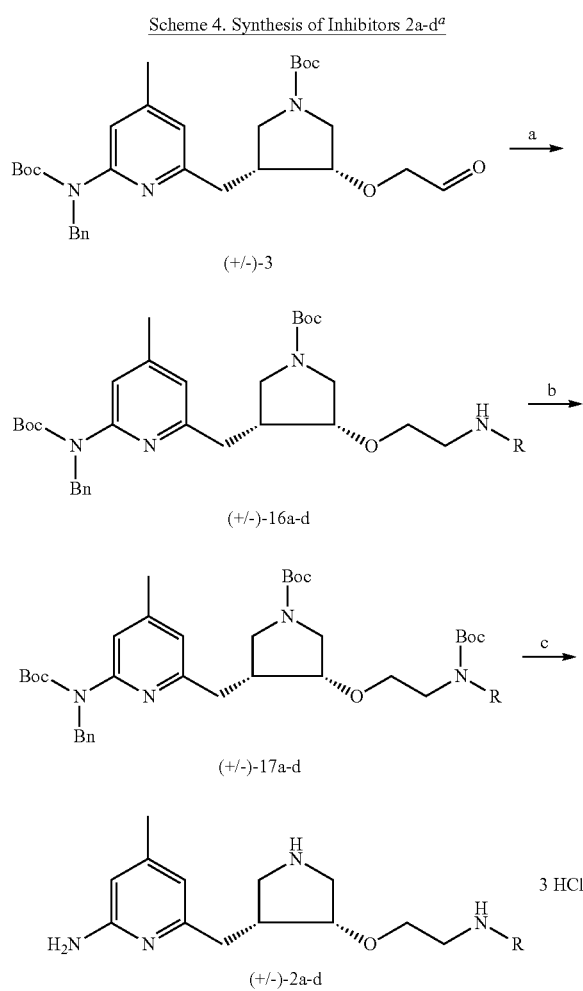

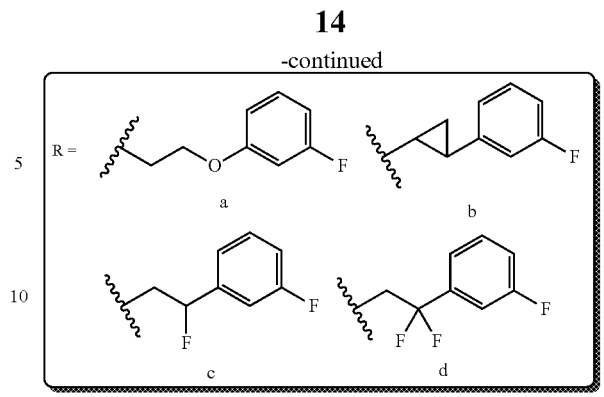

[a]Reagents and conditions: (a) (i) 4a-d, THF, r.t., 5 min, (ii) NaHB(OAc)$_3$, r.t., 3 h; (b) (Boc)$_2$O, Et$_3$N, MeOH, r.t., 12 h, 48-60% for two steps; (c) Pd(OH)$_2$/C, H$_2$, 2:1 EtOH/HCl (12N), r.t., 500 psi, 40 h, 85-91%.

Alternatively, as a variation on the aforementioned embodiments, enantiomerically-pure inhibitors can be prepared, examples of which are shown below. (As a departure from the aforementioned general numbering format, the following compounds 4-10 are illustrated in Schemes 5-8 (and described in examples 43-57) en route to several non-limiting representative variations of inhibitor compound 2d; for instance, enantiomerically difluoromethylene inhibitors 2da-2dd in Scheme 6, below.

Synthesis of enantiomerically pure pyrrolidine core (4a-b) is shown in Scheme 5. First, the racemic trans-alcohol 5 underwent a Mitsunobu reaction using (S)-(−) camphanic acid as a nucleophile to produce two separable diastereomers (6a and 6b) in excellent yields. Next, the ester linkage in 6a and 6b was hydrolyzed in aqueous Na$_2$CO$_3$ to generate 4a and 4b in high yields.

Scheme 5. Synthesis of 4a-b[a]

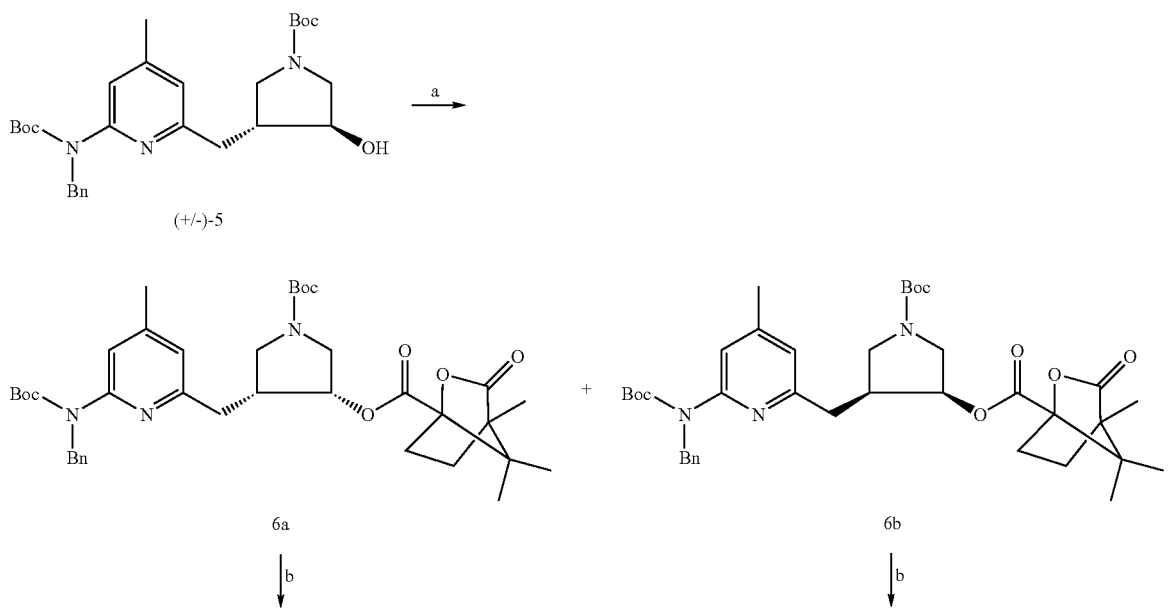

15

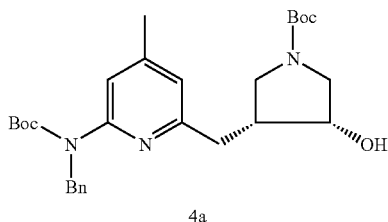

4a

16

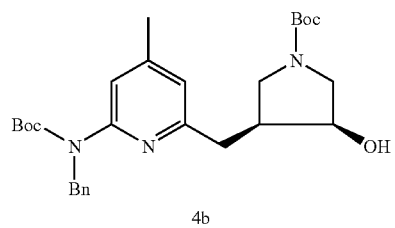

4b

-continued

<sup>a</sup>Reagents and conditions: (a) (S)-(-) camphanic acid, PPh₃, DIAD, rt, 16 h, 95%; (d) Na₂CO₃, rt, 4 h, 95%.

As shown in Scheme 6, single enantiomer 4a or 4b was treated with NaH, and the resulting anion was allowed to react with allyl bromide to generate 7a and 7b in excellent yields. Ozonolysis of 7a and 7b using Zn dust as reducing reagent yielded 8a and 8b in good yields. Aldehydes 8a or 8b were subjected to reductive amination reactions with different ethanamines in the presence of NaHB(OAc)₃ to generate secondary amines, which were further protected by another Boc-protecting group to produce the fully protected inhibitors 9a-d in good yields. Next, the benzyl-protecting group was removed by a catalytic hydrogenation reaction using Pd(OH)₂ at 60° C. to provide 10a-d in modest yields. Finally, the three Boc-protecting groups were removed at the same time in HCl to generate inhibitors 2da-2dd in high yields.

Scheme 6. Synthesis of 3a-d<sup>a</sup>

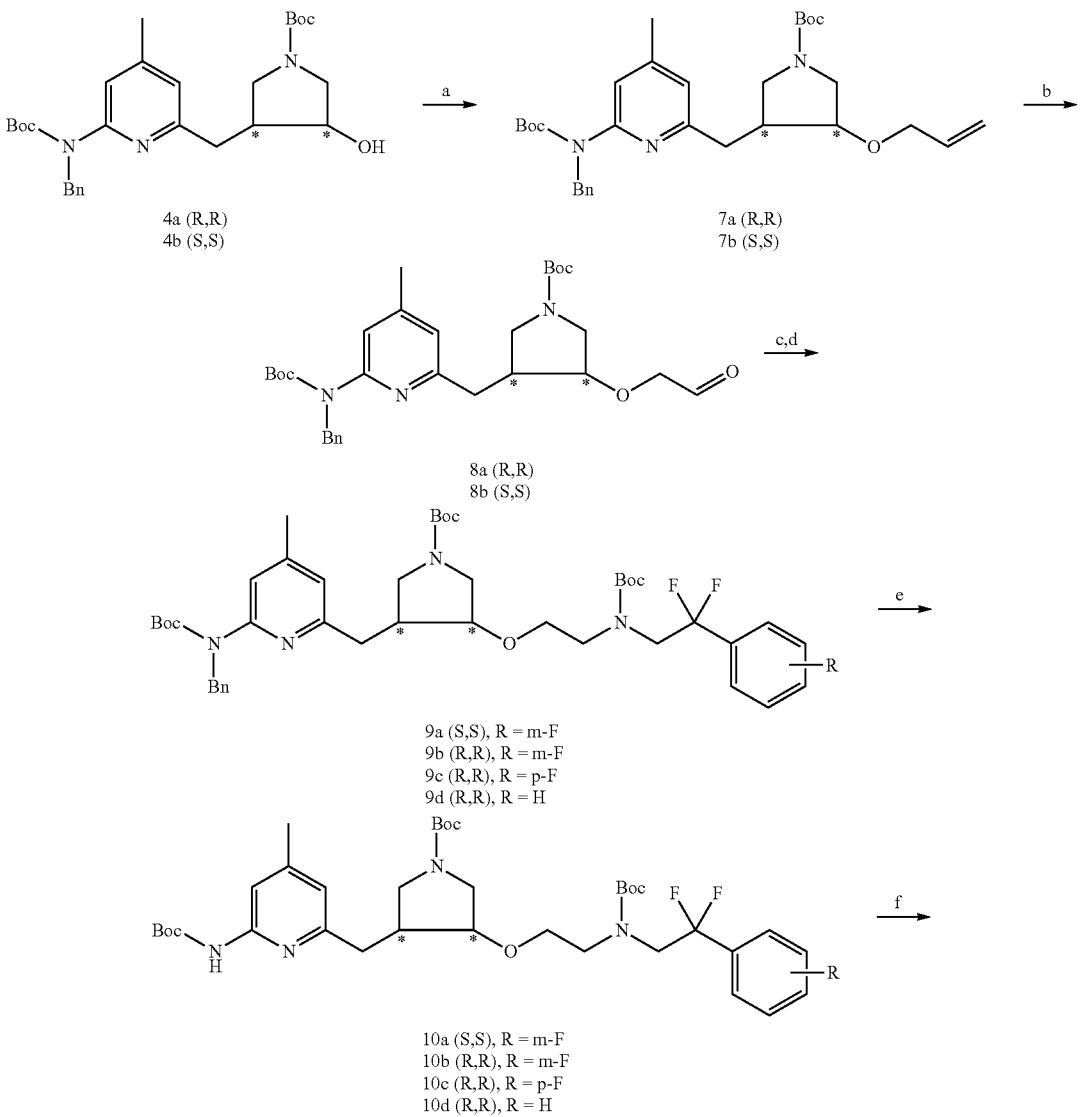

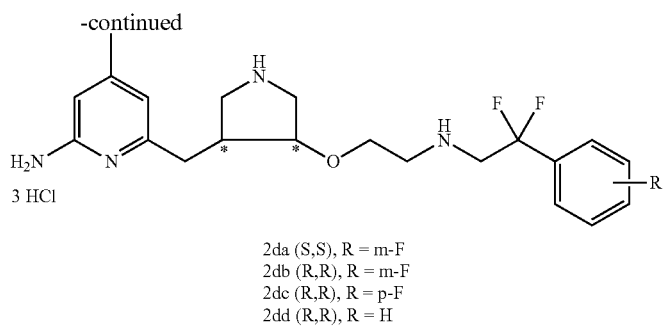

2da (S,S), R = m-F
2db (R,R), R = m-F
2dc (R,R), R = p-F
2dd (R,R), R = H

[a]Reagents and conditions: (a) (i) NaH, (ii) allyl bromide, rt, 1 h, 96%; (b) O$_3$, -78° C., (ii) Zn, -78° C. to rt, 2 h, 81%; (c) (i) ethanamines, THF, r.t., 5 min, (ii) NaHB(OAc)$_3$, r.t., 3 h; (d) (Boc)$_2$O, Et$_3$N, MeOH, r.t., 3 h, 48-60% for two steps; (e) Pd(OH)$_2$/C, H$_2$, EtOH, 60° C., 30 h, 45-60%; (f) 6N HCl/MeOH (2:1), r.t., 16 h, 100%.

As relates to the binding studies discussed below, inhibitor compounds 2e-f were also prepared. The synthesis of inhibitor 2e began with 9a (Scheme 7). Catalytic hydrogenation of 9a using Pd(OH)$_2$ at accelerated temperature removed the benzyl-protecting group, and at the same time, the pyridinyl ring was reduced to generate 10e in modest yields. Then, three Boc-protecting groups were removed in HCl to generate inhibitor 2e in high yields.

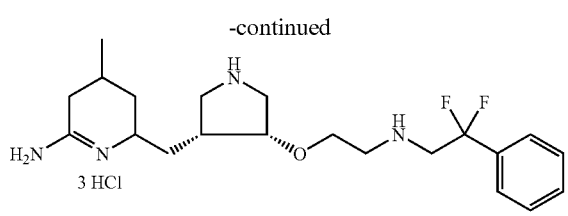

2e

[a]Reagents and conditions: (a) Pd(OH)$_2$/C, H$_2$, EtOH, 60° C., 48 h, 55%; (d) 6N HCl/MeOH (2:1), r.t., 16 h, 96%.

The synthesis of inhibitor 2f is shown in Scheme 8. Reductive amination of aldehyde 8b with 2,2-difluoro-2-(pyridin-2-yl)ethanamine (e.g., as prepared as described above) generated a secondary amine, which was further protected by another Boc-protecting group to provide 9f in good yields. Next, catalytic hydrogenation of 9f removed the benzyl protecting group, and also reduced the pyridinyl group adjacent to the CF$_2$ group to generate 10f in modest yields. Finally, the three Boc-protecting groups were removed at the same time in HCl to generate the final inhibitor 2f in high yields.

Scheme 7. Synthesis of 2e[a]

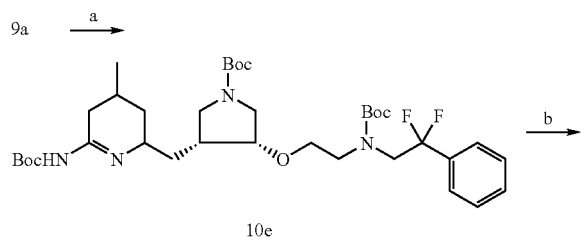

10e

Scheme 8. Synthesis of 2f[a]

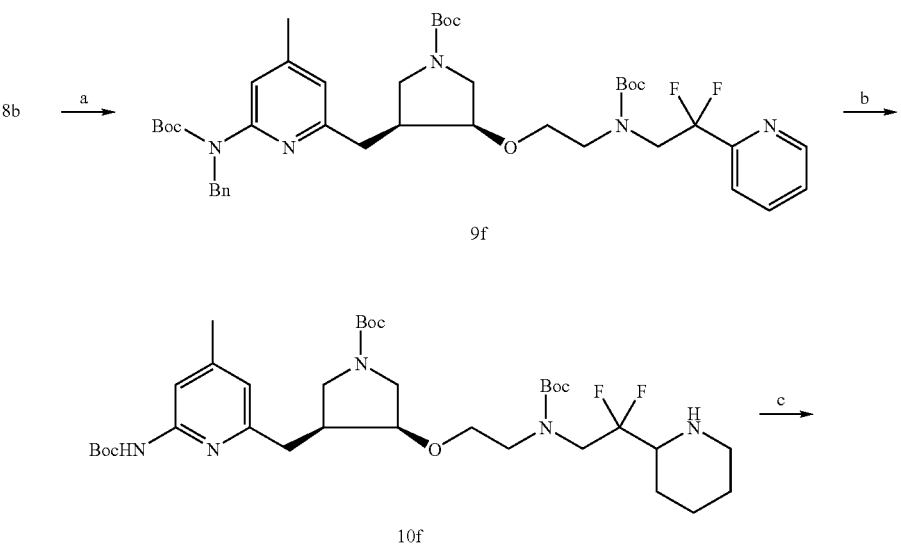

-continued

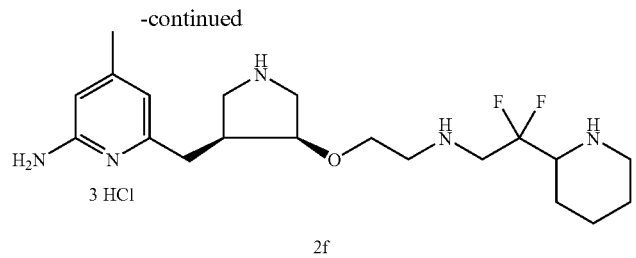

2f

<sup>a</sup>Reagents and conditions: (a) (i) 2,2-difluoro-2-(pyridin-2-yl)ethanamine, THF, r.t., 5 min, (ii) NaHB(OAc)$_3$, r.t., 3 h; (b) (Boc)$_2$O, Et$_3$N, MeOH, r.t., 3 h, 55% for two steps; (c) Pd(OH)$_2$/C, H$_2$, EtOH, 60° C., 30 h, 60%; (d) 2N HCl/MeOH (1:1), r.t., 16 h, 100%.

Crystal Structures of nNOS Bound with Inhibitor Compounds 2da-2dd and 2e-f

Figure 2A:
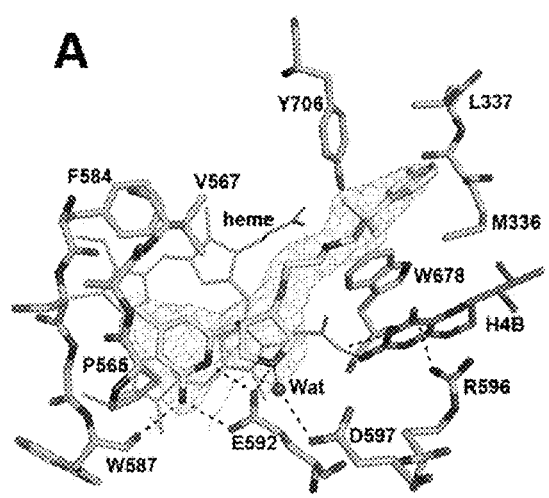
FIGS. 2 A-B. The nNOS active site with inhibitor 2da (A) or 2db (B) bound. The sigmaA weighted 2Fo–Fc density for inhibitor is also shown at contour level of 1 σ. Hydrogen bonds are depicted with dashed lines. Alternate conformations for 2db and E592 were observed.
Figure 2B:
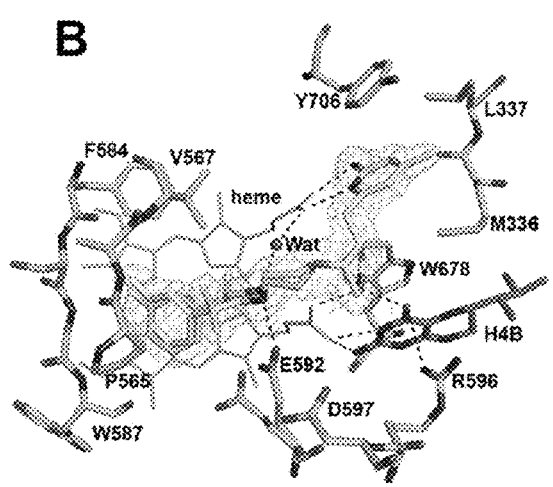

Consistent with the binding preference of the enantiomerically pure parental compound 1, the binding mode of these difluorine derivatives was found also to be dependent on the configuration around the two chiral centers: the 3' and 4' positions of the pyrrolidine ring. While the (S,S) inhibitor 2da was found to bind with its aminopyridine moiety hydrogen bonded to the side chain of Glu592 in nNOS (FIG. 2A), the (R,R) inhibitor 2db adopted a 'flipped' binding mode with its aminopyridine making bifurcated hydrogen bonds with the heme propionate off pyrrole ring D (FIG. 2B). To leave room for these new hydrogen bonds, the Tyr706 side chain rotates away and stacks against the aminopyridine ring of inhibitor. The pyrrolidine nitrogen in 2db also makes favorable hydrogen bonds with propionate A as well as the O4 atom of H$_4$B. In comparison, the pyrrolidine nitrogen in 2da was only loosely hydrogen bonded to Glu592. The long, flexible linker extending from the pyrrolidine allowed the tail fluorophenyl group in 2db to reach the vicinity of Glu592 and to stack against the heme plane. The amino group adjacent to the CF$_2$ moiety points toward the Glu592 side chain, causing the formation of an alternate conformation of the carboxylate to make a hydrogen bond between the amino nitrogen and the carboxylate oxygen (FIG. 2B). This alternate conformation of Glu592 was not observed in structure of nNOS bound with 2da because the tight bifurcated hydrogen bonds from the inhibitor aminopyridine to the carboxylate of Glu592 made a perfect match to the original conformation of the Glu side chain. The fit of the fluorophenyl group in 2db to the site of Glu592 is not that ideal and in order to avoid close van der Waals contacts with the inhibitor, Glu592 adopts an alternate conformation. In addition, the fluorophenyl tail part of 2db is disordered as indicated by the weak electron density for this group. When only one conformation of the tail was modeled with the two fluorine atoms pointing away from the heme plane, strong negative difference density was clustered around fluorine atoms. Also, the electron density of the fluorophenyl ring could not be accounted for with only one ring orientation. The tail portion of 2db was, therefore, modeled with two different conformations (0.6 and 0.4 occupancy) as shown in FIG. 2B. There is a partially occupied water molecule bridging between the heme propionate and the amino group in the tail portion of 2db in its minor conformation. In contrast, the fluorophenyl ring in 2da fit in a pocket surrounded by Met336, Leu337, and Tyr706 (FIG. 2A), but the density for 2da was clear only up to the position of the two fluorine atoms but too poor toward the end to give a definite fluorophenyl ring orientation.

Inhibitor 2dc has its fluorine position in the phenyl ring changed from the meta- in 2db to the para-position. This new position of fluorine makes the tail portion a bit longer in 2dc than in 2db, which resulted in a conformation with the two fluorine atoms pointing downward to the heme plane (FIG. 3A). This conformation disrupts the hydrogen bond between the inhibitor amino group and Glu side chain seen in the major conformation in 2db, but similar to its minor conformation.

Inhibitor 2dd is a derivative of 2db and differs only by the absence of the fluorine on the phenyl ring. Its binding mode to nNOS is, therefore, almost identical to that of 2db (FIG. 3B). Without the fluoro group the phenyl ring makes a looser contact with the hydrophobic pocket defined by Pro565, Val567, and Phe584. The phenyl tail portion in 2db exhibits two alternate conformations similar to what is observed for 2db.

Inhibitor 2e has its aminopyridine ring partially reduced from that in 2dd, which has a negligible impact on the binding mode of the inhibitor compared to 2dd (FIG. 3C). The amino and the ring nitrogens remain planar and are still tightly hydrogen bonded to the heme propionate off pyrrole D and the pyrrolidine nitrogen hydrogen bonded to propionate A and H$_4$B. As in 2db and 2dd, the phenyl tail in 2e shows two conformations above the heme plane while the Glu592 side chain has two conformations, correspondingly.

Another (S,S) inhibitor, 2f, is similar to 2da except the fluorophenyl tail has been replaced by a piperidine ring. The binding of 2f is similar to 2da with its aminopyridine hydrogen bonded to the Glu592 side chain while the piperidine ring fits to the pocket of Met336, Leu337, and Tyr706 (FIG. 3D). The density for the tail portion is good only up to the CF$_2$ moiety with the piperidine partially disordered. Therefore, the orientation of the ring (position of nitrogen) is not well defined.

Crystal Structures of eNOS Bound with Inhibitor Compounds 2db and 2f

Figure 4A:
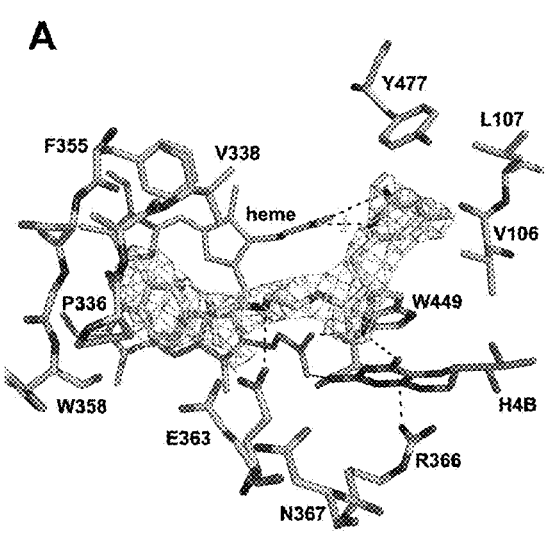
FIGS. 4A-B. The eNOS active site with 2db (A) and 2f (B) bound. Around each inhibitor is the sigmaA weighted 2Fo–Fc density contoured at 1 σ. Major hydrogen bonds are depicted with dashed lines. As observed with nNOS, alternate conformations for Glu363 occur in the eNOS-2db structure.

The eNOS structure bound with the (R,R) inhibitor 2db (FIG. 4A) adopted a 'flipped' binding mode, the same orientation as in nNOS. The Tyr477 side chain rotates out, but is farther away in eNOS and therefore does not experience optimized π-stacking interactions with the aminopyridine of inhibitor observed in nNOS. Similar to what was seen in nNOS, the aminopyridine in 2db makes bifurcated hydrogen bonds with the heme propionate off pyrrole ring D, while the pyrrolidine nitrogen makes favorable hydrogen bonds with propionate A as well as the O4 atom of H$_4$B (FIG. 4A). A hydrogen bond between the inhibitor amino group with alternate conformations for Glu363 also is observed. With the available density at the limited resolution only one conformation of the fluorophenyl tail portion can be modeled.

Figure 4B:
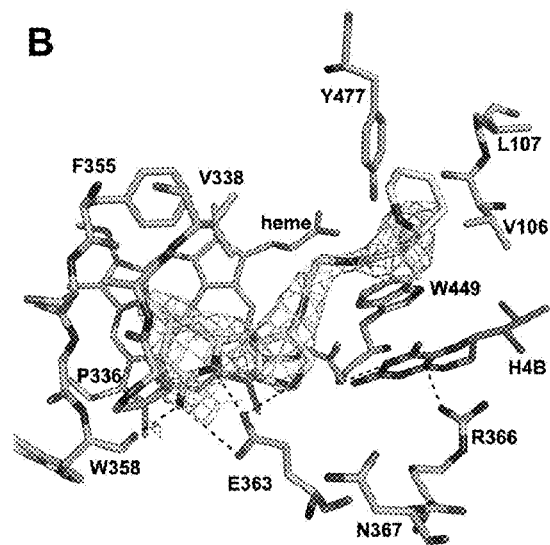

The binding of the (S,S) inhibitor 2f in eNOS is similar to nNOS, with its aminopyridine hydrogen bonded to the Glu363 side chain (FIG. 4B) in the standard binding mode.

The pyrrolidine nitrogen also hydrogen bonds with the conserved glutamate residue, but the density for the tail portion is good only up to the $CF_2$ moiety with the piperidine partially disordered. Therefore, the orientation of the ring (position of nitrogen) and the exact configuration of the puckered ring are not clear.

Inhibitors 2a-d were evaluated for in vitro inhibition against three isozymes of NOS: rat nNOS, bovine eNOS and murine iNOS using known methods. (Hevel, J. M.; Marletta, M. A. Nitric-oxide synthase assays. *Method Enzymol.* 1994, 233, 250-258) Inhibitor 2a, with an electronegative oxygen atom inserted into the lipophilic tail of 1, has $K_i$ values of 86 nM, 21 µM, and 18 µM for nNOS, eNOS, and iNOS, respectively (Table 2). Compared to the lead compound (I), inhibitor 2a is almost six-fold less potent, while the selectivity of this inhibitor for nNOS over eNOS and iNOS decreases by ten fold and three fold, respectively. There may be two considerations with respect to these results. First, compound 2a is one atom longer than 1, which probably makes it too long to fit snugly into the active site of nNOS. Moreover, it has been shown previously that the positively charged amine functionality in the lipophilic tail plays an important role for tight binding of 1 to nNOS, therefore, partial removal of the positive charge from this group may impair the activity of inhibitors Inhibitor 2b, with a cyclopropyl functionality in the lipophilic tail is more potent and selective than 2a, retaining the high potency and selectivity of 1. Inhibitor 2c, with monofluoromethylene adjacent to the basic amino group, shows even better potency for nNOS and excellent selectivity for nNOS over eNOS and iNOS. Finally, inhibitor 2d, with a difluoromethylene in the lipophilic tail of 1, exhibited a 2.2-fold drop in potency relative to 2c. The introduction of the strongly electron-withdrawing difluoromethylene group can significantly remove the positive charge on the amino group in the lipophilic tail, which decreases its ability for electrostatic interaction with the heme carboxylate. However, inhibitor 2d still showed very good selectivity for nNOS over eNOS and iNOS.

TABLE 2

$K_i^a$ Values of Inhibitors for rat nNOS, bovine eNOS, and murine iNOS.

| Compound | nNOS (µM) | eNOS (µM) | iNOS (µM) | selectivity[b] n/e | n/i |
|---|---|---|---|---|---|
| 1[11] | 0.015 | 31 | 9.5 | 2100 | 630 |
| 2a | 0.086 | 21 | 18 | 240 | 210 |
| 2b | 0.046 | 68 | 11 | 1500 | 220 |
| 2c | 0.036 | 36 | 13 | 1000 | 360 |
| 2d | 0.080 | 62 | 52 | 780 | 650 |

[a]The $K_i$ values were calculated based on the directly measured $IC_{50}$ values, which represent at least duplicate measurements with standard deviations of ±10%.
[b]The ratio of $K_i$ (eNOS or iNOS) to $K_i$ (nNOS).

From the foregoing, the three best inhibitors (2b, 2c, and 2d) from this group of embodiments were chosen, together with compound (I), to test their potency in a cell-based assay. This assay can provide valuable data about membrane permeability. The results are summarized in Table 3. The $IC_{50}$ values of inhibitors 2b, 2c, and 2d are comparable to that of compound 1. The ratios of inhibition of purified nNOS versus the cell-based assay ($IC_{50}/IC_{50(cell)}$) were calculated, which indicate the relative membrane permeability of different inhibitors (Table 3). The $IC_{50}/IC_{50(cell)}$ values of all three low $pK_a$ inhibitors are higher than compound 1, which indicates that by partially removing the positive charge on the amino group in 1, inhibitors with improved cell permeability can be achieved. Specifically, inhibitor 2b shows a 2.4-fold increase through cells membrane permeation relative to 1, while inhibitors 2c and 2d exhibited 1.7-fold and 2.0-fold increased penetration, respectively. A comparison of the $IC_{50}/IC_{50(cell)}$ values between 2c and 2d demonstrates that the stronger difluoromethylene electron-withdrawing group, which significantly decreased the $pK_a$ compared to the monofluoromethylene group, greatly improved cell permeability.

TABLE 3

$IC_{50}$ values of inhibitors in purified enzyme assay and cell-based assay.

| compound | $IC_{50}$ (µM)[a] | $IC_{50(cell)}$ (µM)[a] | $IC_{50}/IC_{50(cell)} \times 10^{-2}$ |
|---|---|---|---|
| 1 | 0.13 | 7 | 1.8 |
| 2b | 0.4 | 9 | 4.4 |
| 2c | 0.31 | 10 | 3.1 |
| 2d | 0.7 | 19 | 3.6 |

[a]The $IC_{50}$ values represent at least duplicate measurements with standard deviations of ±10%.

TABLE 4

$K_i^a$ values of inhibitors for rat nNOS, bovine eNOS, and murine iNOS.

| Compound | nNOS (µM) | eNOS (µM) | iNOS (µM) | selectivity[b] n/e | n/i |
|---|---|---|---|---|---|
| 2d | 0.080 | 62 | 52 | 780 | 650 |
| 2da | 0.390 | 110 | 130 | 280 | 330 |
| 2db | 0.036 | 140 | 51 | 3800 | 1400 |
| 2dc | 0.160 | 31 | 190 | 190 | 1200 |
| 2dd | 0.085 | 130 | 85 | 1500 | 1000 |
| 2e | 0.170 | 130 | 26 | 770 | 150 |
| 2f | 2.70 | 64 | 450 | 24 | 170 |

[a]The $K_i$ values were calculated based on the directly measured $IC_{50}$ values, which represent at least duplicate measurements with standard deviations of ±10%.
[b]The ratio of $K_i$ (eNOS or iNOS) to $K_i$ (nNOS).

Inhibitory Assays and Structure-Based Evaluation

To continue the study, inhibitors 2da-2dd and 2e-2f were evaluated for in vitro inhibition activities against three isozymes of NOSs including rat nNOS, bovine eNOS and murine iNOS (see, Havel, supra) as summarized in Table 4. Compared to the racemic compound 2d, the (S,S) enantiomer 2da is a weak inhibitor for nNOS with the $K_i$ values of 390 nM, which is five-fold less potent than 2d. In addition, the selectivity of this inhibitor for nNOS over eNOS and iNOS also decreases by 3-fold and 2-fold, respectively. The (R,R) enantiomer 2db, however, shows excellent potency for nNOS ($K_i$=36 nM) and remarkable selectivity over eNOS (3800-fold) and iNOS (1400-fold). These results indicate that the chirality around the cis-chiral pyrrolidine core plays a key role in determining the potency and selectivity of inhibitors, as we have observed for another series of trans- or cis-chiral pyrrolidine inhibitors (1). The potency and selectivity shown with the racemic compound 2d can be attributed mainly to the (R,R) component 2db. We now know that a large difference in binding affinity between 2da and 2db originates from two different binding modes. (1) The flipped binding mode of 2db relative to 2da allows both aminopyridine and pyrrolidine nitrogen atoms to make extensive hydrogen bonds with the heme and $H_4B$ (FIG. 2B). In addition, as we have argued elsewhere, (1) the conformation of 2da when bound to NOS places the pyrrolidine N atom very close to the aminopyridine and owing to electrostatic repulsion, this aminopyridine is only partially protonated. However, in the 2db flipped orientation the aminopyridine is farther from the pyrrolidine N atom and remains fully protonated. Thus, the 2db conformation provides greater electrostatic stabilization than the 2da conformation which accounts for the 10-fold lower $K_i$ of 2db than 2da.

As a p-fluorophenyl derivative of 2db, inhibitor 2dc shows a significant drop in potency for nNOS ($K_i$=160 nM), which is 4.5-fold less potent than 2db. More interestingly, 2dc also loses most of the selectivity over eNOS and iNOS of 2db by moving one single F atom from the m-position to the p-position of the phenyl tail. The new fluorine position leads to a 'difluorine-down' binding mode of the inhibitor's phenyl tail. As a result, the hydrogen bond between the Glu592 side chain and the amino nitrogen in the tail seen in 2db has been eliminated, which may explain the weaker potency of 2dc.

Inhibitor 2dd, with the substituent F atom removed from the phenyl tail, has restored good potency for nNOS ($K_i$=85 nM) and high isozyme-selectivity (1500-fold over eNOS and 1000-fold over iNOS). This is because 2dd has retained the binding mode of 2db. The only difference is that without a fluorine on the phenyl ring the van der Waals contacts to the protein (Pro565, Val567, and Phe584) are less optimal compared to that for 2db. This results in a bit less potency and selectivity for 2dd than 2db.

The amidino inhibitor 2e, with the aromatic system of the aminopyridine fragment partially reduced, exhibits a 2-fold drop in potency against nNOS compared to 2dd. This result demonstrates that π-π stacking in 2dd between the aromatic aminopyridine ring and the Tyr706 side chain contributes to its tighter binding. Moreover, the removal of the aromatic system of the aminopyridine ring from inhibitor 2dd makes 2e binds more than 3-fold better to iNOS thus exhibiting a much less selectivity.

Finally, inhibitor 2f, with a (S,S) configuration of the pyrrolidine core and a piperidinyl tail, showed poor inhibition activity and isozyme-selectivity. Both 2da and 2f have a similar binding orientation and rather poor potency among the inhibitors reported in this work. This result emphasizes again that the chirality of the pyrrolidine core is the key to higher inhibitory activity with (R,R) inhibitors. In addition, a less polar aromatic ring such as the fluoro-phenyl group in 2da seems to fit better in to the pocket surrounded by Met336, Leu337, and Tyr706 in nNOS than does the polar piperidinyl ring in 2f. However, both 2da and 2f bind to eNOS with similar potency possibly because of the smaller Val106 side chain in the pocket in eNOS compared to Met336 in nNOS.

Isoform selection from the inhibitors in Table 4 is not a straightforward structure-based determination. For instance, for any particular inhibitor among those reported in Table 4 the binding mode in eNOS is no different from that seen in nNOS. As discussed for another series of chiral pyrrolidine containing inhibitors, one of the potential reasons for the isoform selectivity shown by 2db is the difference in stacking interaction between the aminopyridine and Tyr706 in nNOS (or Tyr 477 in eNOS). It has been consistently observed that tighter interactions between this Tyr and the aminopyridine with nNOS complexed with inhibitors that adopt the 2db flipped orientation. (Data not presented herein.)

In part, as demonstrated above, the present invention provides a new series of selective nNOS inhibitors (e.g., 2da-2dd and 2e-2f) with monocationic character and, therefore, better bioavailability. Biological evaluation of these new inhibitors based on crystal structures suggests, for instance, use of inhibitor 2db, which not only retains most of the inhibitory activity of the compound 2d, but also shows remarkable selectivity for nNOS over both eNOS and iNOS. Accordingly, this invention represents an advancement toward the goal of developing drugs with therapeutic potential in treatment of diseases caused by unregulated NO generation from nNOS.

EXAMPLES OF THE INVENTION

The following non-limiting examples and data illustrate various aspects and features relating to the compounds, compositions and/or methods of the present invention, including the preparation and use of various selective neuronal nitric oxide synthase inhibitors, as are available through the synthetic methodologies described herein. In comparison with the prior art, the present compounds, compositions and/or methods provide results and data which are surprising, unexpected and contrary thereto. While the utility of this invention is illustrated through use of several compounds and moieties, groups or substituents (e.g., halide, alkyl, etc.) thereof, it will be understood by those skilled in the art that comparable results are obtainable with various other compounds and moieties/groups/substituents (e.g., substituted alkyl, etc.), as are commensurate with the scope of this invention and would be understood by those skilled in the art and made aware of this invention—using synthetic techniques of the sort described herein or in the incorporated references or straight-forward modifications thereof, such techniques limited only by available reagents and starting materials.

All syntheses were conducted under anhydrous conditions in an atmosphere of argon, using flame-dried apparatus and employing standard techniques in handling air sensitive materials. All solvents were distilled and stored under an argon or nitrogen atmosphere before using. All reagents were used as received. Aqueous solutions of sodium bicarbonate, sodium chloride (brine), and ammonium chloride were saturated. Analytical thin layer chromatography was visualized by ultraviolet, ninhydrin, or phosphomolybdic acid (PMA). Flash column chromatography was carried out under a positive pressure of nitrogen. $^1$H NMR spectra were recorded on 500 MHz spectrometers. Data are presented as follows: chemical shift (in ppm on the δ scale relative to δ=0.00 ppm for the protons in TMS), integration, multiplicity (s=singlet, d=doublet, t=triplet, q=quartet, m=multiplet, br=broad), coupling constant (J/Hz). Coupling constants were taken directly from the spectra and are uncorrected. $^{13}$C NMR spectra were recorded at 125 MHz, and all chemical shift values are reported in ppm on the δ scale, with an internal reference of δ 77.0 or 49.0 for CDCl$_3$ or MeOD, respectively. High-resolution mass spectra were measured on liquid chromatography/time of flight mass spectrometry (LC-TOF).

Characterization of New Compounds

Example 1

(E)-Methyl 3-(3-fluorophenyl)acrylate (6). To a solution of (E)-3-(3-fluorophenyl)acrylic acid (5, 6.0 g, 32.7 mmol) in MeOH (150 mL) at 0° C. was added concentrated H$_2$SO$_4$ (3.0 mL) slowly. The reaction was heated under reflux for 24 h then cooled to room temperature and neutralized with Na$_2$CO$_3$ (1.0 g). The solvent was removed by rotary evaporation and the resulting yellow oil partitioned between EtOAc (300 mL) and saturated NaHCO$_3$ (300 mL). The aqueous layer was extracted with EtOAc (2×100 mL). The combined organic layers were washed with brine (200 mL) and dried over Na$_2$SO$_4$. The solvent was removed by rotary evaporation to yield 6 as a low melting (<25° C.) white solid (32.0 mmol, 99%): $^1$H NMR (500 MHz, CDCl$_3$) δ 3.79 (s, 3H), 6.39-6.43 (d, J=16.0 Hz, 1H), 7.04-7.07 (dt, J=2.0, 8.0 Hz, 1H), 7.18-

7.20 (d, J=9.0 Hz, 1H), 7.25-7.26 (d, J=8.0 Hz, 1H), 7.30-7.35 (m, 1H), 7.60-7.64 (d, J=16.0 Hz, 1H); $^{13}$C NMR (125 MHz, CDCl$_3$) δ 52.0, 114.4, 114.6, 117.3, 117.4, 119.4, 124.29, 124.32, 130.6, 130.7, 136.8, 136.9, 143.6, 143.7, 162.2, 164.2, 167.2; LCQ-MS (M+H$^+$) calcd for C$_{10}$H$_{10}$FO$_2$ 181. found 181.

Example 2

Methyl 2-(3-fluorophenyl)cyclopropanecarboxylate (7). To a solution of KOH (2.5 g, 45 mmol) in H$_2$O (4 mL) in a Mini Diazald apparatus (Aldrich Z108898) was added dropwise 2-(2-ethoxyethoxy)ethanol (14.0 mL) and ether (8.0 mL). To the condenser of the apparatus was attached a round-bottom receiving flask (Caution: this flask must have a clear-seal joint). The receiving flask was put in a Dry Ice-acetone bath. A glass tube (Caution: this tube must have fire-polished ends) was attached to the side arm of the apparatus, which ended in an ether (~5 mL) trap in a Dry Ice-acetone bath. A separate clear-seal-joint funnel was placed over the reaction vessel. This funnel was charged with a solution of Diazald (5.0 g, 23 mmol) in ether (30 mL). The reaction vessel was warmed slowly to 65° C. The Diazald solution was added slowly to the reaction vessel over a period of 20 min. Afterward, additional ether (10 mL) was added to the reaction vessel through the top funnel at the same temperature. The distillation was continued until the yellow distillate became colorless.

To a flame-dried round-bottom flask containing ether (50 mL) and CH$_2$Cl$_2$ (150 mL) was added 6 (900 mg, 5.0 mmol) and Pd(OAc)$_2$ (5.80 mg) at 0° C. To this flask was added the freshly prepared diazomethane solution through a cannula, and then the reaction solution was slowly warmed to room temperature over a period of 30 min and allowed to stir at room temperature for an additional 2 h. The reaction mixture was washed with H$_2$O (150 mL) and brine (150 mL) and dried over NaSO$_4$. The solvent was removed by rotary evaporation to yield 7 as a colorless oil (965 mg, 5.0 mmol, 100%): $^1$H NMR (500 MHz, CDCl$_3$) δ 1.30-1.35 (ddd, J=5.0, 7.0, 8.5 Hz, 1H), 1.60-1.66 (dt, J=5.0, 10.0 Hz, 1H), 1.90-1.94 (ddd, J=4.0, 5.0, 8.5 Hz, 1H), 2.51-2.54 (dt, J=2.5, 5.5 Hz, 1H), 3.74 (s, 3H), 6.70-6.80 (td, J=2.0, 10.0 Hz, 1H), 6.90-6.95 (m, 2H), 7.23-7.28 (m, 1H); $^{13}$C NMR (125 MHz, CDCl$_3$) δ 17.4, 24.4, 26.1, 52.3, 113.2, 113.4, 113.6, 113.8, 122.2, 130.1, 130.2, 142.9, 143.0, 164.2, 173.8; LCQ-MS (M+H$^+$) calcd for C$_{11}$H$_{12}$FO$_2$ 195. found 195.

Example 3

2-(3-Fluorophenyl)cyclopropanecarboxylic acid (8). To a solution of 7 (390 mg, 2.0 mmol) in MeOH (5 mL) was added 2N NaOH (5 mL) slowly. The reaction solution was stirred at room temperature for 2 h then diluted with H$_2$O (25 mL). After extraction with ether (20 mL), the aqueous layer was acidified with 2N HCl (2.1 mL). The resulting solution was extracted with ether (3×40 mL). The combined organic layers were dried over MgSO$_4$ and concentrated to give 8 (325 mg, 1.8 mmol, 99%) as a light yellow oil: $^1$H NMR (500 MHz, CDCl$_3$) δ 0.87-0.91 (dd, J=6.0, 13.5 Hz, 1H), 1.21-1.29 (m, 1H), 1.39-1.43 (ddd, J=5.0, 6.5, 8.0 Hz, 1H), 1.67-1.72 (m, 1H), 1.90-1.94 (m, 1H), 2.58-2.63 (m, 1H), 6.79-6.82 (dd, J=2.0, 5.5 Hz, 1H), 6.90-6.95 (m, 2H), 7.24-7.28 (m, 1H), 8.90-11.00 (br s, 1H); $^{13}$C NMR (125 MHz, CDCl$_3$) δ 17.8, 24.4, 26.9, 31.8, 113.3, 113.5, 113.8, 114.0, 122.30, 122.32, 130.2, 130.3, 142.4, 142.5, 162.2, 164.2, 179.8; LCQ-MS (M−H$^+$) calcd for C$_{10}$H$_8$FO$_2$ 179. found 179.

Example 4 tent-Butyl 2-(3-fluorophenyl)cyclopropylcarbamate (9). To a solution of 8 (300 mg, 1.67 mmol) in dry t-BuOH (5.0 mL) was added diphenyl phosphorazidate (DPPA, 400 μL, 1.83 mmol) and triethylamine (Et$_3$N, 350 μL, 2.51 mmol). The reaction solution was allowed to stir at 85° C. for two days, then cooled to room temperature and concentrated. The resulting solution was partitioned between ether (30 mL) and saturated NaHCO$_3$ (30 mL). The aqueous layer was extracted with ether (2×30 mL). The combined organic layers were dried over Na$_2$SO$_4$ and concentrated. The crude product was purified by flash chromatography to yield 9 (325 mg, 1.30 mmol, 82%) as a white solid: $^1$H NMR (500 MHz, CDCl$_3$) δ 1.10-1.25 (m, 2H), 1.40-1.55 (m, 10H), 2.00-2.10 (br s, 1H), 2.73 (br s, 1H), 5.04 (br s, 1H), 6.82-6.88 (m, 2H), 6.92-6.94 (d, J=7.5 Hz, 1H), 7.20-7.25 (dd, J=7.5, 14.0 Hz, 1H); $^{13}$C NMR (125 MHz, CDCl$_3$) δ 16.6, 25.1, 28.6, 32.9, 113.0, 113.2, 113.4, 113.6, 122.4, 129.9, 130.0, 130.1, 143.77, 143.83, 162.2, 164.1; LCQ-MS (M+H$^+$) calcd for C$_{14}$H$_{19}$FNO$_2$ 252. found 252.

2-(3-Fluorophenyl)cyclopropanamine trifluoroacetic acid salt (4b). To a solution of 9 (560 mg, 2.2 mmol) in CH$_2$Cl$_2$ (15 mL) was added trifluoroacetic acid (15 mL). The reaction mixture was stirred at room temperature for 30 min. The solvent was removed by rotary evaporation. The yellow oil was put under vacuum for 24 h to give crude amine 4b (579 mg, 2.2 mmol, 100%) as a yellow oil, which was used in the next step without further purification: $^1$H NMR (500 MHz, CDCl$_3$) δ 1.10-1.30 (br s, 1H), 1.40-1.60 (br s, 1H), 2.30-2.50 (br s, 1H), 2.70-2.90 (br s, 1H), 6.70-6.72 (m, 1H), 6.72-6.77 (m, 1H), 6.89-7.00 (m, 1H), 7.10-7.30 (m, 1H), 7.80-8.20 (br s, 2H), 10.8-11.8 (br s, 1H); $^{13}$C NMR (125 MHz, CDCl$_3$) δ 13.2, 21.5, 31.6, 113.5, 113.7, 114.2, 114.4, 122.29, 122.31, 130.4, 130.5, 140.1, 140.2, 162.2, 164.1; LCQ-MS (M+H$^+$) calcd for C$_9$H$_{11}$FN 152. found 152; LC-TOF (M+H$^+$) calcd for C$_9$H$_{11}$FN 152.08755. found 152.08703.

Examples 5-29 can be considered in the context of Schemes 1b-1e, above.

Example 5

General Method (A) for Rhodium (II)-catalyzed cyclopropanation. To a solution of styrene derivative 4a-c (20 mmol) in dry toluene (40 mL) was added catalyst Rh$_2$(OAc)$_4$ (0.4 mmol). The resulting mixture was heated at 80° C. for 30 min, then EtO$_2$CCHN$_2$ (10 mmol) was added dropwise at the same temperature over a period of 1 h. The reaction mixture was allowed to stir at 85° C. for an additional 2 h, and then cooled to room temperature. The solvent was removed by rotary evaporation and the resulting oil was purified by flash chromatography (1-10% EtOAc in hexanes) to generate 5a-c as mixtures of cis/trans isomers.

Example 6

General Method (B) for Epimerization and hydrolysis. To a solution of 5a-c (10 mmol) in EtOH (10 mL) was added NaOMe (40 mL) in portion. The reaction solution was heated under reflux for 40 h, and then concentrated by rotary evaporation. The resulting residue was partitioned between DCM (200 mL) and H$_2$O (100 mL). The aqueous layer was extracted with DCM (2×100 mL). The combined organic layers were dried over Na$_2$SO$_4$ and concentrated. The crude ethyl ester was taken up in MeOH (70 mL), to which was added LiOH (345 mg, 15 mmol) and H$_2$O (70 mL). The reaction was heated at 70° C. for 16 h. After cooling to room temperature, MeOH was removed by rotary evaporation. The resulting aqueous solution was acidified by concentrated HCl to pH 1, which was extracted with EtOAc (3×150 mL). The combined organic layers were dried over $Na_2SO_4$, and concentrated. The crude product was purified by flash chromatography to yield 6a-c (75-80%) as white solids.

Example 7

General Method (C) for Curtius rearrangement. To a solution of 6a-c (2.0 mmol) in dry t-BuOH (0.3 M) was added diphenyl phosphorazidate (2.2 mmol) and TEA (3.0 mmol). The reaction solution was heated at 85° C. for two days, then cooled to room temperature and concentrated. The resulting solution was partitioned between ether (50 mL) and $NaHCO_3$ (50 mL). The aqueous layer was extracted with ether (2×50 mL). The combined organic layers were dried over $Na_2SO_4$ and concentrated. The crude product was purified by flash chromatography to yield 7a-c (75-82%) as white solids.

Example 8

General Method (D) for Boc-deprotection. To a solution of 7a-c (1.0 mmol) in $CH_2Cl_2$ (5 mL) was added TFA (5 mL). The reaction mixture was stirred at room temperature for 30 min. The solvent was removed by rotary evaporation. The yellow oil was put under vacuum for 24 h to give crude amine 3a-c as yellow oils, which was used in the next step without further purification.

Example 9

General Method (E) for Reductive amination. To a solution of aldehyde (0.1 mmol) in DCM (3 mL) was added amine (0.11 mmol), followed by TEA (0.2 mmol), and $NaHB(OAc)_3$ (0.12 mmol). The mixture was stirred at room temperature for an additional 3 h, and then concentrated. The crude product was purified by flash column chromatography (EtOAc/hexanes, 2:1-4:1) to give the product as colorless oil.

Example 10

General Method (F) for Boc-deprotection of Inhibitor Compound. To a solution of tri-Boc-protected inhibitor (0.2 mmol) in MeOH (0.5 mL) was added 6 N HCl (1.0 mL). The reaction mixture was sit at room temperature for 16 h, and then concentrated. The resulting pale yellow oil was put under vacuum for 30 h to give final inhibitors (95-99%).

Example 11

2-m-Tolylcyclopropanecarboxylic acid (6a). Compound 6a was synthesized using general method A and B (77%): $^1$H NMR (500 MHz, $CDCl_3$) δ 1.30-1.40 (ddd, J=4.5, 7.0, 7.5 Hz, 1H), 1.60-1.65 (dd, J=5.0, 9.0 Hz, 1H), 1.85-1.90 (ddd, J=4.5, 5.0, 7.5 Hz, 1H), 2.50-2.60 (ddd, J=4.5, 7.0, 9.0 Hz, 1H), 6.85-6.95 (m, 1H), 7.00-7.05 (m, 1H), 7.15-7.22 (m, 2H); $^{13}$C NMR (125 MHz, $CDCl_3$) δ 17.5, 21.4, 24.0, 27.1, 123.2, 127.0, 127.4, 128.4, 138.2, 139.4, 180.1; LCQ-MS (M−H$^+$) calcd for $C_{11}H_{13}O_2$ 177. found 177.

Example 12

2-(3-Clorophenyl)cyclopropanecarboxylic acid (6b). Compound 6b was synthesized using general method A and B (80%): $^1$H NMR (500 MHz, $CDCl_3$) δ 1.30-1.40 (ddd, J=2.0, 3.5, 7.0 Hz, 1H), 1.60-1.65 (dd, J=5.0, 9.0 Hz, 1H), 1.85-1.91 (m, 1H), 2.50-2.60 (m, 1H), 6.85-7.02 (m, 1H), 7.05-7.10 (m, 1H), 7.15-7.22 (m, 2H); $^{13}$C NMR (125 MHz, $CDCl_3$) δ 17.8, 24.4, 26.9, 31.8, 113.3, 113.5, 113.8, 114.0, 122.30, 122.32, 130.2, 130.3, 142.4, 142.5, 162.2, 164.2, 179.8; LC-MS (M−H$^+$) calcd for $C_{10}H_{10}ClO_2$ 197. found 197.

Example 13

2-(3-Fluorophenyl)cyclopropanecarboxylic acid (6c). Compound 6c was synthesized using general method A and B (75%): $^1$H NMR (500 MHz, $CDCl_3$) δ 0.87-0.91 (dd, J=6.0, 13.5 Hz, 1H), 1.21-1.29 (m, 1H), 1.39-1.43 (ddd, J=5.0, 6.5, 8.0 Hz, 1H), 1.67-1.72 (m, 1H), 1.90-1.94 (m, 1H), 2.58-2.63 (m, 1H), 6.79-6.82 (dd, J=2.0, 5.5 Hz, 1H), 6.90-6.95 (m, 2H), 7.24-7.28 (m, 1H), 8.90-11.00 (br s, 1H); $^{13}$C NMR (125 MHz, $CDCl_3$) δ 17.8, 24.4, 26.9, 31.8, 113.3, 113.5, 113.8, 114.0, 122.30, 122.32, 130.2, 130.3, 142.4, 142.5, 162.2, 164.2, 179.8; LCQ-MS (M−H$^+$) calcd for $C_{10}H_8FO_2$ 179. found 179.

Example 14 tert-Butyl 2-m-tolylcyclopropylcarbamate (7a). Compound 7a was synthesized using general method C (82%): $^1$H NMR (500 MHz, $CDCl_3$) δ 1.00-1.20 (m, 2H), 1.46 (s, 9H), 1.95-2.05 (ddd, J=3.0, 6.5, 9.5 Hz, 1H), 2.31 (s, 3H), 2.74 (br s, 1H), 4.85 (br s, 1H), 6.91-6.93 (m, 2H), 6.97-6.99 (d, J=7.5 Hz, 1H), 7.13-7.16 (dd, J=7.5, 8.0 Hz, 1H); $^{13}$C NMR (125 MHz, $CDCl_3$) δ 16.3, 21.4, 24.5, 28.4, 32.6, 120.2, 120.3, 123.4, 126.1, 126.8, 127.2, 128.2, 130.1, 137.9, 140.6; LCQ-MS (M+H$^+$) calcd for $C_{15}H_{21}NO_2$ 248. found 248.

Example 15 tert-Butyl 2-(3-chloroluorophenyl)cyclopropylcarbamate (7b). Compound 7b was synthesized using general method C (77%): $^1$H NMR (500 MHz, $CDCl_3$) δ 1.14-1.17 (dd, J=6.5, 7.0 Hz, 2H), 1.45 (s, 9H), 1.99-2.03 (ddd, J=2.5, 7.5, 10.5 Hz, 1H), 2.72 (br s, 1H), 4.88 (br s, 1H), 6.95-7.02 (d, J=7.0 Hz, 1H), 7.10-7.25 (m, 3H); $^{13}$C NMR (125 MHz, $CDCl_3$) δ 16.3, 24.5, 28.4, 32.6, 120.1, 120.3, 124.8, 126.2, 126.6, 129.5, 129.9, 134.1, 142.9; LCQ-MS (M+H$^+$) calcd for $C_{14}H_{19}ClNO_2$ 268. found 268.

Example 16 tert-Butyl 2-(3-fluorophenyl)cyclopropylcarbamate (7c). Compound 7c was synthesized using general method C (75%): $^1$H NMR (500 MHz, $CDCl_3$) δ 1.10-1.25 (m, 2H), 1.40-1.55 (m, 10H), 2.00-2.10 (br s, 1H), 2.73 (br s, 1H), 5.04 (br s, 1H), 6.82-6.88 (m, 2H), 6.92-6.94 (d, J=7.5 Hz, 1H), 7.20-7.25 (dd, J=7.5, 14.0 Hz, 1H); $^{13}$C NMR (125 MHz, $CDCl_3$) δ 16.6, 25.1, 28.6, 32.9, 113.0, 113.2, 113.4, 113.6, 122.4, 129.9, 130.0, 130.1, 143.77, 143.83, 162.2, 164.1; LCQ-MS (M+H$^+$) calcd for $C_{14}H_{19}FNO_2$ 252. found 252.

Example 17

Compounds 8a and 8b. To a solution of amine 3c (450 mg, 3.0 mmol) in DCM was added camphanic chloride (650 mg, 3.0 mmol), followed by TEA (510 μL, 3.75 mmol). The reaction was allowed to stir at room temperature for 30 min, and then concentrated. The resulting oil was purified by flash chromatography (EtOAc/Hexanes, 1:4) to generate 8a (445 mg, 45%): $^1$H NMR (500 MHz, $CDCl_3$) δ 0.92 (s, 3H), 1.12 (s, 6H), 1.19-1.22 (m, 1H), 1.28-1.30 (m, 2H), 1.65-1.75 (m, 1H), 1.85-2.00 (m, 2H), 2.05-2.15 (m, 1H), 2.50-2.60 (m, 1H), 2.90-2.98 (m, 1H), 6.68 (br s, 1H), 6.84-6.90 (m, 2H), 6.95-6.97 (d, J=7.5 Hz, 1H), 7.21-7.25 (m, 1H); $^{13}$C NMR (125 MHz, CDCl$_3$) δ 9.7, 15.8, 16.5, 16.7, 24.67, 24.78, 29.0, 30.3, 31.6, 54.0, 55.3, 92.4, 113.1, 113.27, 113.32, 113.5, 122.30, 122.32, 129.8, 129.9, 142.6, 142.7, 162.0, 163.9, 168.3, 178.2; LC-TOF (M+H$^+$) calcd for C$_{19}$H$_{23}$FNO$_3$ 332.1662. found 332.1673; and 8b (360 mg, 36%): $^1$H NMR (500 MHz, CDCl$_3$) δ 0.91 (s, 3H), 1.11 (s, 6H), 1.20-1.35 (m, 3H), 1.65-1.75 (m, 1H), 1.85-2.00 (m, 2H), 2.00-2.10 (m, 1H), 2.50-2.58 (m, 1H), 2.89-2.95 (m, 1H), 6.67 (br s, 1H), 6.84-6.90 (m, 2H), 6.95-6.97 (d, J=8.0 Hz, 1H), 7.21-7.24 (m, 1H); $^{13}$C NMR (125 MHz, CDCl$_3$) δ 9.7, 16.0, 16.5, 16.7, 24.61, 24.63, 29.0, 30.3, 31.5, 54.0, 55.3, 92.38, 92.40, 113.1, 113.29, 113.32, 113.4 113.5, 113.6, 122.30, 122.32, 129.8, 129.9, 142.66, 142.72, 162.0, 163.9, 168.2, 168.3, 178.2; LC-TOF (M+H$^+$) calcd for C$_{19}$H$_{23}$FNO$_3$ 332.1662. found 332.1677.

Example 18

(1S,2R)-2-(3-Fluorophenyl)cyclopropanamine (3d). To a solution of 8a (330 mg, 1.0 mmol) in EtOH (5 mL) was slowly added 12 N HCl (10 mL). The resulting mixture was heated under reflux for 72 h and then cooled to room temperature. The solvent was removed by rotary evaporation, and the resulting crude material was purified with flash chromatography (2-5% MeOH in DCM) to give 3d as a yellow oil (105 mg, 70%): $^1$H NMR (500 MHz, CDCl$_3$) δ 1.10-1.30 (br s, 1H), 1.40-1.60 (br s, 1H), 2.30-2.50 (br s, 1H), 2.70-2.90 (br s, 1H), 6.70-6.72 (m, 1H), 6.72-6.77 (m, 1H), 6.89-7.00 (m, 1H), 7.10-7.30 (m, 1H), 7.80-8.20 (br s, 2H); $^{13}$C NMR (125 MHz, CDCl$_3$) δ 13.2, 21.5, 31.6, 113.5, 113.7, 114.2, 114.4, 122.29, 122.31, 130.4, 130.5, 140.1, 140.2; LC-TOF (M+H$^+$) calcd for C$_9$H$_{11}$FN 152.0876. found 152.0870.

Example 19

(1R,2S)-2-(3-Fluorophenyl)cyclopropanamine (3e). 3e was synthesized using a similar procedure to that of 3d using 8b as a starting material (67%): $^1$H NMR (500 MHz, CDCl$_3$) δ 1.10-1.30 (br s, 1H), 1.40-1.60 (br s, 1H), 2.30-2.50 (br s, 1H), 2.70-2.90 (br s, 1H), 6.70-6.72 (m, 1H), 6.72-6.77 (m, 1H), 6.89-7.00 (m, 1H), 7.10-7.30 (m, 1H), 7.80-8.20 (br s, 2H); $^{13}$C NMR (125 MHz, CDCl$_3$) δ 13.2, 21.5, 31.6, 113.5, 113.7, 114.2, 114.4, 122.29, 122.31, 130.4, 130.5, 140.1, 140.2; LC-TOF (M+H$^+$) calcd for C$_9$H$_{11}$FN 152.0876. found 152.0870.

Example 20

(3R,4R)-tert-Butyl 3-((6-(bis(tert-butoxycarbonyl)amino)-4-methylpyridin-2-yl)methyl)-4-(2-((1S,2R/1R,2S)-2-m-tolylcyclopropylamino)ethoxy)pyrrolidine-1-carboxylate (9a). Compound 9a was synthesized using general method D (87%): $^1$H NMR (500 MHz, CDCl$_3$) δ 0.90-0.97 (m, 1H), 1.00-1.05 (m, 1H), 1.40-1.45 (m, 27H), 1.84-1.91 (m, 1H), 2.27-2.32 (m, 6H), 2.33-2.40 (m, 1H), 2.60-2.75 (m, 1H), 2.75-2.83 (m, 1H), 2.85-2.93 (m, 2H), 2.95-3.00 (m, 1H), 3.05-3.15 (m, 1H), 3.25-3.30 (m, 1H), 3.31-3.34 (m, 1H), 3.35-3.55 (m, 1H), 3.57-3.74 (m, 1H), 3.75-3.85 (m, 1H), 6.85-6.95 (m, 4H), 6.92-7.01 (m, 2H), 7.10-7.20 (m, 2H); $^{13}$C NMR (100 MHz, CDCl$_3$) δ 13.7, 14.1, 14.2, 17.2, 17.3, 17.4, 19.1, 20.9, 21.0, 21.1, 21.4, 22.2, 24.96, 24.99, 25.0, 25.5, 27.9, 28.5, 29.7, 30.6, 34.6, 34.7, 41.0, 41.1, 42.6, 43.2, 48.8, 48.9, 49.0, 49.1, 50.3, 60.4, 64.4, 68.4, 78.6, 79.2, 79.3, 79.4, 82.8, 82.9, 119.5, 119.6, 122.7, 122.8, 122.9, 126.3, 126.5, 126.6, 126.7, 126.8, 128.17, 128.24, 128.3, 128.5, 128.6, 132.0, 132.1, 137.8, 137.9, 141.3, 142.3, 149.6, 151.4, 151.5, 151.8, 154.8, 159.1, 159.2, 171.2; LC-TOF (M+H$^+$) calcd for C$_{38}$H$_{57}$N$_4$O$_7$ 681.4227. found 681.4224.

Example 21

(3R,4R)-tert-Butyl 3-((6-(bis(tert-butoxycarbonyl)amino)-4-methylpyridin-2-yl)methyl)-4-(2-((1S,2R/1R,2S)-2-(3-clorophenyl)cyclopropylamino)ethoxy)pyrrolidine-1-carboxylate (9b). Compound 9b was synthesized using general method D (87%): $^1$H NMR (500 MHz, CDCl$_3$) δ 0.92-0.99 (m, 1H), 1.07-1.11 (m, 1H), 1.40-1.45 (m, 27H), 1.85-1.90 (m, 1H), 2.29-2.33 (m, 3H), 2.34-2.38 (m, 1H), 2.60-2.75 (m, 1H), 2.76-2.83 (m, 1H), 2.85-2.93 (m, 2H), 2.95-3.00 (m, 1H), 3.05-3.15 (m, 1H), 3.25-3.30 (m, 1H), 3.31-3.34 (m, 1H), 3.35-3.52 (m, 1H), 3.57-3.74 (m, 1H), 3.75-3.85 (m, 1H), 6.85-6.92 (m, 2H), 6.93-7.05 (m, 2H), 7.08-7.20 (m, 4H); $^{13}$C NMR (100 MHz, CDCl$_3$) δ 17.4, 17.5, 17.6, 18.7, 20.9, 21.0, 22.2, 24.9, 25.0, 25.3, 26.2, 27.9, 28.5, 34.6, 34.7, 35.6, 41.3, 41.4, 41.5, 41.6, 42.5, 43.1, 48.7, 48.8, 49.1, 50.3, 52.0, 68.4, 68.5, 76.7, 78.6, 79.2, 79.3, 79.4, 82.8, 82.9, 119.5, 119.6, 122.7, 124.0, 124.07, 124.10, 124.12, 124.3, 125.5, 125.6, 125.7, 125.81, 125.83, 125.86, 125.94, 128.5, 128.6, 129.4, 129.5, 129.6, 132.0, 132.1, 134.1, 134.2, 143.6, 144.6, 144.7, 149.6, 151.47, 151.53, 151.8, 154.8, 159.7; LC-TOF (M+H$^+$) calcd for C$_{37}$H$_{53}$ClN$_4$O$_7$ 701.3681. found 701.3884.

Example 22

(3R,4R)-tert-Butyl 3-((6-(bis(tert-butoxycarbonyl)amino)-4-methylpyridin-2-yl)methyl)-4-(2-((1S,2R/1R,2S)-2-(3-fluorophenyl)cyclopropylamino)ethoxy)pyrrolidine-1-carboxylate (9c). Compound 9c was synthesized using general method D (81%): $^1$H NMR (500 MHz, CDCl$_3$) δ 0.95-1.00 (m, 1H), 1.06-1.10 (m, 1H), 1.40-1.46 (m, 27H), 1.86-1.90 (m, 1H), 2.26-2.33 (m, 3H), 2.35-2.40 (m, 1H), 2.60-2.75 (m, 1H), 2.76-2.85 (m, 1H), 2.86-2.92 (m, 2H), 2.95-2.98 (m, 1H), 3.05-3.13 (m, 1H), 3.24-3.30 (m, 1H), 3.30-3.35 (m, 1H), 3.36-3.51 (m, 1H), 3.57-3.75 (m, 1H), 3.77-3.85 (m, 1H), 6.85-6.92 (m, 2H), 6.93-7.20 (m, 4H); $^{13}$C NMR (100 MHz, CDCl$_3$) δ 17.4, 17.5, 17.6, 18.7, 20.9, 21.0, 22.2, 24.9, 25.0, 25.3, 26.2, 27.9, 28.5, 34.6, 34.7, 35.6, 41.3, 41.4, 41.5, 41.6, 42.5, 43.1, 48.7, 48.8, 49.1, 50.3, 52.0, 68.4, 68.5, 76.7, 78.6, 79.2, 79.3, 79.4, 82.8, 82.9, 119.5, 119.6, 122.7, 124.0, 124.07, 124.10, 124.12, 124.3, 125.5, 125.6, 125.7, 125.81, 125.83, 125.86, 125.94, 128.5, 128.6, 129.4, 129.5, 129.6, 132.0, 132.1, 134.1, 134.2, 143.6, 144.6, 144.7, 149.6, 151.47, 151.53, 151.8, 154.8, 159.7; LC-TOF (M+H$^+$) calcd for C$_{43}$H$_{60}$F$_3$N$_4$O$_8$ 685.3977. found 685.3991.

Example 23

(3R,4R)-tert-Butyl 3-((6-(bis(tert-butoxycarbonyl)amino)-4-methylpyridin-2-yl)methyl)-4-(2-((1S,2R)-2-(3-fluorophenyl)cyclopropylamino)ethoxy)pyrrolidine-1-carboxylate (9d). Compound 9d was synthesized using general method D (82%): $^1$H NMR (500 MHz, CDCl$_3$) δ 0.95-1.01 (m, 1H), 1.10-1.15 (m, 1H), 1.40-1.45 (m, 27H), 1.89-1.92 (m, 1H), 2.28-2.32 (m, 3H), 2.33-2.37 (m, 1H), 2.60-2.75 (m, 1H), 2.76-2.83 (m, 1H), 2.85-2.93 (m, 2H), 2.95-3.00 (m, 1H), 3.05-3.15 (m, 1H), 3.27-3.31 (m, 1H), 3.32-3.34 (m, 1H), 3.35-3.55 (m, 1H), 3.57-3.74 (m, 1H), 3.75-3.85 (m, 1H), 6.65-6.72 (m, 1H), 6.80-6.89 (m, 2H), 6.90-6.95 (m, 2H), 7.15-7.20 (m, 1H); $^{13}$C NMR (100 MHz, CDCl$_3$) δ 14.2, 17.4, 17.5, 21.0, 22.7, 24.7, 24.8, 27.9, 28.5, 29.7, 31.6, 34.6, 34.7, 36.6, 41.4, 41.5, 42.5, 43.1, 44.7, 48.7, 48.8, 49.1, 50.3, 50.9, 60.4, 68.3, 78.6, 79.2, 79.3, 79.4, 82.8, 82.9, 112.2, 112.4, 112.6, 119.5, 119.6, 121.6, 122.7, 128.5, 128.6, 129.6, 129.7, 131.9, 132.0, 132.1, 132.2, 149.6, 151.5, 151.8, 154.6, 154.8, 159.0, 159.1, 162.0, 163.9; LC-TOF (M+H$^+$) calcd for $C_{37}H_{54}FN_4O_7$ 685.3977. found 685.3979.

Example 24

4-Methyl-6-(((3R,4R)-4-(2-((1S,2R/1R,2S)-2-m-tolylcyclopropylamino)ethoxy)pyrrolidin-3-yl)methyl)pyridin-2-amine (2a). Inhibitor 2a was synthesized using general method E as a mixture of two diastereomers (90%): $^1$H NMR (500 MHz, D$_2$O) δ 1.10-1.30 (m, 1H), 1.35-1.45 (m, 1H), 2.10-2.15 (m, 3H), 2.15-2.20 (m, 3H), 2.20-2.50 (m, 1H), 2.50-2.80 (m, 2H), 2.81-3.00 (m, 2H), 3.19-3.25 (m, 1H), 3.30-3.40 (m, 2H), 3.47-3.52 (m, 1H), 3.55-3.70 (m, 1H), 3.71-3.85 (m, 1H), 4.00-4.15 (m, 1H), 6.35-6.60 (m, 2H), 6.85-6.90 (m, 2H), 6.91-7.15 (m, 2H); $^{13}$C NMR (125 MHz, D$_2$O) δ 12.2, 12.3, 15.1, 20.2, 20.4, 20.5, 20.6, 20.7, 21.0, 21.6, 23.2, 28.8, 28.9, 30.1, 30.5, 31.8, 37.4, 38.5, 41.2, 41.3, 47.0, 47.2, 47.5, 49.2, 49.3, 63.6, 64.5, 78.1, 78.3, 110.2, 110.3, 113.9, 114.0, 122.9, 123.1, 123.3, 126.3, 126.5, 126.6, 126.7, 126.8, 127.5, 127.6, 127.7, 128.6, 128.7, 128.78, 128.82, 128.9, 129.0, 131.8, 131.9, 137.9, 138.1, 138.7, 138.9, 139.0, 145.59, 145.62, 153.8, 158.1; LC-TOF (M+H$^+$) calcd for $C_{21}H_{30}FN_4O_2$ 381.2654. found 381.2653.

Example 25

6-(((3R,4R)-4-(2-((1S,2R/1R,2S)-2-(3-Clorophenyl)cyclopropylamino)ethoxy)pyrrolidin-3-yl)methyl)-4-methylpyridin-2-amine (2b). Compound 2b was synthesized using general method E as a mixture of two diastereomers (91%): $^1$H NMR (500 MHz, D$_2$O) δ 1.10-1.30 (m, 1H), 1.35-1.50 (m, 1H), 2.15-2.20 (m, 3H), 2.25-2.30 (m, 1H), 2.35-2.50 (m, 1H), 2.55-2.70 (m, 2H), 2.70-2.77 (m, 1H), 2.81-3.00 (m, 2H), 3.19-3.25 (m, 1H), 3.30-3.40 (m, 1H), 3.49-3.52 (m, 1H), 3.55-3.70 (m, 1H), 3.75-3.85 (m, 1H), 4.05 (br s, 0.5H), 4.12 (br s, 0.5H), 6.34 (s, 0.5H), 6.39 (s, 0.5H), 6.51 (s, 0.5H), 6.53 (s, 0.5H), 6.95-7.01 (m, 1H), 7.05-7.20 (m, 3H); $^{13}$C NMR (125 MHz, D$_2$O) δ 12.3, 12.4, 12.6, 20.3, 20.4, 20.5, 21.1, 28.8, 28.9, 30.6, 37.4, 38.6, 41.2, 41.3, 47.0, 47.1, 47.2, 47.5, 49.2, 49.3, 63.5, 64.5, 78.2, 78.4, 110.31, 110.34, 113.9, 114.0, 124.7, 124.75, 124.82, 126.1, 126.16, 126.23, 126.7, 126.9, 127.0, 130.0, 130.1, 130.2, 133.8, 133.9, 134.0, 140.2, 140.7, 145.52, 145.54, 153.8, 158.1; LC-TOF (M+H$^+$) calcd for $C_{22}H_{30}ClN_4O$ 401.2108. found 401.2093.

Example 26

6-(((3R,4R)-4-(2-((1S,2R/1R,2S)-2-(3-Fluorophenyl)cyclopropylamino)ethoxy)pyrrolidin-3-yl)methyl)-4-methylpyridin-2-amine (2c). Compound 2c was synthesized using general method E as a mixture of two diastereomers (99%): $^1$H NMR (500 MHz, D$_2$O) δ 1.30-1.40 (m, 1H), 1.41-1.48 (m, 1H), 2.10-2.20 (m, 3H), 2.30-2.50 (m, 1H), 2.51-2.77 (m, 2H), 2.80-2.90 (m, 1H), 2.91-3.03 (m, 1H), 3.04-3.40 (m, 3H), 3.41-3.72 (m, 2H), 3.73-3.88 (m, 1H), 3.90-4.11 (m, 1H), 4.40-4.50 (m, 1H), 6.30-6.60 (m, 2H), 6.70-6.90 (m, 2H), 7.00-7.20 (m, 2H); $^{13}$C NMR (125 MHz, D$_2$O) δ 12.6, 12.9, 20.7, 20.9, 21.2, 21.4, 29.1, 37.7, 37.8, 38.6, 41.5, 45.3, 47.3, 47.6, 47.7, 49.6, 63.8, 64.5, 78.3, 78.5, 109.0, 110.5, 113.2, 113.4, 113.8, 114.0, 114.3, 122.4, 127.2, 128.1, 129.2, 130.1, 136.4, 140.7, 140.9, 145.9, 146.6, 153.0, 154.0, 158.3, 161.8, 163.8; LC-TOF (M+H$^+$) calcd for $C_{21}H_{30}FN_4O_2$ 385.2404. found 385.2393.

Example 27

6-(((3R,4R)-4-(2-((1S,2R)-2-(3-Fluorophenyl)cyclopropylamino)ethoxy)pyrrolidin-3-yl)methyl)-4-methylpyridin-2-amine (2d). Compound 2d was synthesized using general method E (95%): $^1$H NMR (500 MHz, D$_2$O) δ 1.30-1.40 (m, 1H), 1.41-1.46 (m, 1H), 2.18 (s, 3H), 2.19-2.20 (m, 1H), 2.40-2.50 (m, 1H), 2.55-2.70 (m, 2H), 2.81-3.00 (m, 3H), 3.19-3.23 (dd, J=3.5, 13.5 Hz, 1H), 3.30-3.40 (m, 2H), 3.49-3.52 (m, 1H), 3.55-3.61 (m, 1H), 3.75-3.85 (m, 1H), 4.06 (br s, 1H), 6.38 (s, 1H), 6.54 (s, 1H), 6.80-6.95 (m, 3H), 7.15-7.25 (dd, J=5.5, 10.5 Hz, 1H); $^{13}$C NMR (125 MHz, D$_2$O) δ 12.6, 20.4, 21.0, 28.8, 30.1, 38.4, 41.3, 47.1, 47.5, 49.3, 64.3, 78.3, 110.3, 112.9, 113.1, 113.6, 113.8, 114.0, 122.1, 128.9, 129.0, 130.4, 130.5, 131.8, 131.9, 133.1, 140.6, 140.7, 145.6, 153.9, 158.1; LC-TOF (M+H$^+$) calcd for $C_{21}H_{30}FN_4O_2$ 385.2404. found 385.2384.

Example 28

(3S,4S)/(3R,4R)-tert-Butyl 3-((6-(benzyl(tert-butoxycarbonyeamino)-4-methylpyridin-2-yl)methyl)-4-(2-(tert-butoxycarbonyl(2-(3-fluorophenyl)cyclopropyl)amino) ethoxy)pyrrolidine-1-carboxylate (12). To a solution of aldehyde 11 (100 mg, 0.18 mmol) in DCM (2 mL) was added 3e (60 mg, 0.37 mmol), followed by TEA (125 μL, 0.9 mmol). The mixture was allowed to stir at room temperature for 5 min before NaHB(OAc)$_3$ (50 mg, 0.23 mmol) was added. The reaction mixture was stirred for an additional 3 h then partitioned between EtOAc (50 mL) and brine (25 mL). The organic layer was dried over Na$_2$SO$_4$ and concentrated to yield crude secondary amine. To a solution of the resulting crude amine in MeOH (1.5 mL) was added (Boc)$_2$O (120 mg, 0.56 mmol) and Et$_3$N (75 μL, 0.56 mmol). The reaction mixture was stirred at room temperature for 6 h and then partitioned between EtOAc (50 mL) and brine (20 mL). The organic layer was dried over Na$_2$SO$_4$, and the solvents were removed by rotary evaporation. The resulting material was purified by flash column chromatography (EtOAc/hexanes, 1:4-1:2) to yield 12 (70 mg, 60%) as a colorless oil (71%): $^1$H NMR (500 MHz, CDCl$_3$) δ 1.10-1.22 (m, 2H), 1.35-1.50 (m, 28H), 1.65-1.80 (br s, 1H), 2.10-2.20 (br s, 1H), 2.20-2.35 (m, 3H), 2.40-2.80 (m, 3H), 2.80-2.95 (m, 1H), 2.97-3.10 (m, 1H), 3.16-3.21 (m, 1H), 3.22-3.44 (m, 3H), 3.45-3.70 (m, 3H), 4.04-4.10 (m, 1H), 5.10-5.25 (br s, 2H), 6.55-6.65 (m, 1H), 6.65-6.95 (m, 3H), 7.10-7.27 (m, 6H), 6.31-6.45 (m, 1H); $^{13}$C NMR (125 MHz, CDCl$_3$) δ 14.0, 14.4, 14.5, 19.4, 21.3, 21.4, 22.9, 28.4, 28.7, 28.8, 30.0, 30.9, 31.8, 34.8, 34.9, 40.0, 40.1, 42.9, 49.1, 49.5, 50.2, 50.5, 51.1, 60.7, 64.6, 78.2, 79.4, 79.7, 80.2, 81.4, 81.5, 112.9, 113.0, 117.2, 117.3, 120.2, 122.1, 126.8, 127.1, 127.2, 127.3, 128.3, 130.0, 140.1, 148.7, 148.8, 154.1, 154.6, 154.7, 155.0, 157.9, 162.2, 164.1, 171.4, 171.5; LC-TOF (M+H$^+$) calcd for $C_{44}H_{60}FN_4O_7$ 775.4441. found 775.4441.

Example 29

6-(((3S,4S)/(3R,4R)-4-(2-(2-(3-Fluorophenyl)cyclopropylamino)ethoxy)pyrrolidin-3-yl)methyl)-4-methylpyridin-2-amine (10). To a solution of 12 (0.2 mmol) in EtOH (20 mL) was added Pd(OH)$_2$/C (100 mg). The reaction vessel was charged with H$_2$, heated at 60° C. for 30 h, then cooled to room temperature. The catalyst was removed by filtration, and the resulting solution was concentrated by rotary evaporation. The crude material was purified by flash column chromatography (EtOAc/hexanes, 1:4-1:2) to yield 13 as a white foamy solid To a solution of the resulting 13 in MeOH (0.5 mL) was added 6 N HCl (1.0 mL). The reaction mixture was allowed to sit at room temperature for 16 h. The solvent was removed by rotary evaporation. The crude product was recrystallized using cold diethyl ether to provide 10 as a pale yellow solid (20 mg, 25%): $^1$H NMR (500 MHz, D$_2$O) δ 1.18-1.20 (m, 3H), 2.20 (s, 3H), 2.60-2.72 (m, 2H), 2.75-2.90 (m, 2H), 3.00-3.10 (m, 2H), 3.15-3.33 (m, 3H), 3.34-3.42 (m, 1H), 3.44-3.60 (m, 3H), 3.70-3.80 (m, 1H), 4.09 (s, 1H), 6.46-4.67 (m, 1H), 6.56 (s, 1H), 6.90-7.10 (m, 3H), 7.20-7.25 (m, 1H); $^{13}$C NMR (125 MHz, D$_2$O) δ 15.2, 15.5, 21.3, 29.2, 38.4, 38.5, 41.6, 41.7, 44.2, 44.4, 47.3, 49.5, 55.6, 64.0, 64.4, 78.4, 110.6, 114.3, 114.4, 114.5, 116.2, 116.4, 125.4, 125.6, 130.8, 130.9, 138.3, 145.9, 146.0, 154.1, 158.4, 161.9, 163.9; LC-TOF (M+H$^+$) calcd for C$_{22}$H$_{32}$FN$_4$O 387.2560. found 385.2556.

Example 30

1-(2-Bromo-1-fluoroethyl)-3-fluorobenzene (11). To a solution of 3-fluorostyrene (10, 5.0 g, 41 mmol) in CH$_2$Cl$_2$ at 0° C. was added NBS (8.8 g, 49.2 mmol). After 30 min, Et$_3$N.3HF (20 mL, 123 mmol) was added. The reaction solution was warmed to room temperature and stirred for 16 h. The reaction was quenched with saturated NaHCO$_3$ then partitioned between EtOAc (500 mL) and H$_2$O (300 mL). The organic layer was washed with brine (300 mL), dried over Na$_2$SO$_4$, and concentrated. The crude product was purified by flash column chromatography (EtOAc/hexanes, 1:18-1:9) to yield 11 as a colorless liquid (5.8 g, 85%): $^1$H NMR (500 MHz, CDCl$_3$) δ 3.55-3.80 (m, 2H), 5.59-5.61 (dd, J=4.0, 7.0 Hz, 0.5H), 5.68-5.70 (dd, J=4.5, 7.5 Hz, 0.5H), 7.00-7.20 (m, 3H), 7.30-7.50 (m, 1H); $^{13}$C NMR (125 MHz, CDCl$_3$) δ 34.0, 34.3, 91.4, 91.4, 92.8, 113.0, 113.2, 116.3, 116.4, 116.5, 121.6, 121.7, 130.6, 130.7, 139.7, 139.8, 139.9, 162.1, 164.1; GC-MS calcd for C$_8$H$_7$BrF$_2$ 220. found 220.

Example 31

1-(2-Azido-1-fluoroethyl)-3-fluorobenzene (12). To a solution of 11 (2.3 g, 10.5 mmol) in dry DMSO (15 mL) was added NaN$_3$ (1.0 g, 15.7 mmol). The reaction solution was allowed to stir at 65° C. for 4 h then cooled to room temperature. The reaction mixture was partitioned between EtOAc (300 mL) and H$_2$O (200 mL). The organic layer was washed with H$_2$O (200 mL), brine (200 mL), and dried over Na$_2$SO$_4$. The solvents were removed by rotary evaporation and the crude product was purified by flash column chromatography (EtOAc/hexanes, 1:18-1:9) to yield 12 (1.6 g, 85%) as a yellow oil: $^1$H NMR (500 MHz, CDCl$_3$) δ 3.40-3.50 (dd, J=3.0, 13.5, 0.5H), 3.50-3.60 (dd, J=3.0, 13.5 Hz, 0.5H), 3.60-3.75 (m, 1H), 5.50-5.60 (dd, J=3.0, 8.0 Hz, 0.5H), 5.65-5.80 (dd, J=3.0, 8.0 Hz, 0.5H), 7.00-7.20 (m, 3H), 7.30-7.50 (m, 1H); $^{13}$C NMR (125 MHz, CDCl$_3$) δ 55.9, 56.1, 91.82, 91.84, 93.2, 93.3, 112.78, 112.84, 112.96, 113.03, 116.19, 116.20, 116.36, 116.38, 121.24, 121.27, 121.30, 121.33, 130.7, 130.8, 139.09, 139.15, 139.25, 139.31, 162.1, 164.1; GC-MS calcd for C$_8$H$_7$F$_2$N$_3$ 183. found 183.

2-Fluoro-2-(3-fluorophenyl)ethanamine (4c). To a solution of azide 12 (1.8 g,

Example 32

10.0 mmol) in EtOH (30 mL) was added 1 N HCl (15 mL) and Pd(OH)$_2$/C (20%, 200 mg). The reaction mixture was allowed to stir under one atmosphere of H$_2$ for 24 h. The catalyst was removed by filtration, and the solvent was evaporated. The resulting yellowish solid was partitioned between diethyl ether (200 mL) and 1 N HCl (200 mL). The aqueous layer was washed with diethyl ether (200 mL) then concentrated to yield amine 4c as a hydrochloride salt (1.69 g, 8.8 mmol, 98%): $^1$H NMR (500 MHz, D$_2$O) δ 3.33-3.35 (dd, J=3.5, 4.0 Hz, 1H), 3.36-3.39 (dd, J=3.5, 4.0 Hz, 1H), 5.71-5.74 (dd, J=5.0, 6.0 Hz, 0.5H), 5.81-5.83 (dd, J=5.0, 6.0 Hz, 0.5H), 7.05-7.13 (m, 3H), 7.33-7.48 (m, 1H); $^{13}$C NMR (125 MHz, D$_2$O) δ 44.0, 44.2, 89.3, 90.7, 112.67, 112.73, 112.85, 112.92, 116.5, 116.7, 121.57, 121.59, 121.63, 131.1, 131.2, 137.35, 137.45, 137.51, 161.8, 163.8; LCQ-MS (M+H$^+$) calcd for C$_8$H$_{10}$F$_2$N 158. found 158; LC-TOF (M+H$^+$) calcd for C$_8$H$_{10}$F$_2$N 158.07758. found 158.07738.

Example 33

1-(2-Bromo-1,1-difluoroethyl)-3-fluorobenzene (14). To a flask containing 2-bromo-3'-fluoroacetophenone (13, 2.15 g, 10 mmol) was added DAST (1.38 mL, 10.5 mmol). The flask was sealed and the reaction was allowed to proceed at room temperature for seven days. The reaction mixture was partitioned between EtOAc (300 mL) and saturated NaHCO$_3$ (300 mL). The organic layer was washed with brine (300 mL) and dried over Na$_2$SO$_4$. The solvents were removed by rotary evaporation. The crude product was purified by flash column chromatography (EtOAc/hexanes, 1:18-1:9) to yield 14 (1.65 g, 70%) as a brown liquid: $^1$H NMR (500 MHz, CDCl$_3$) δ 3.74-3.80 (t, J=14.0 Hz, 2H), 7.18-7.27 (m, 2H), 7.31-7.34 (m, 1H), 7.44-7.48 (m, 1H); $^{13}$C NMR (125 MHz, CDCl$_3$) δ 33.2, 33.5, 33.8, 113.08, 113.13, 113.28, 113.33, 113.38, 117.87, 117.89, 118.04, 118.06, 118.07, 118.22, 118.24, 121.4, 121.5, 130.7, 130.8, 161.8, 183.8; GC-MS calcd for C$_8$H$_6$BrF$_3$ 238. found 238.

Example 34

1-(2-Azido-1,1-difluoroethyl)-3-fluorobenzene (15). To a solution of 14 (2.4 g, 10 mmol) in anhydrous DMSO (15 mL) was added NaN$_3$ (1.0 g, 15.7 mmol). The reaction solution turned purple upon heating. After being stirred at 110° C. for 8 h, the reaction mixture was cooled to room temperature and partitioned between EtOAc (300 mL) and H$_2$O (200 mL). The organic layer was washed with H$_2$O (200 mL), brine (200 mL), and dried over Na$_2$SO$_4$. The solvents were removed by rotary evaporation. The crude product was purified by flash column chromatography (EtOAc/hexanes, 1:9) to yield azide 15 (1.7 g, 88%) as a yellow oil: $^1$H NMR (500 MHz, CDCl$_3$) δ 3.60-3.75 (m, 2H), 7.00-7.15 (m, 2H), 7.15-7.35 (m, 1H), 7.40-7.60 (m, 1H); $^{13}$C NMR (125 MHz, CDCl$_3$) δ 55.8, 56.1, 56.4, 112.95, 113.01, 113.06, 113.14, 113.19, 113.25, 117.89, 117.90, 118.06, 118.07, 118.08, 119.78, 119.81, 121.25, 121.28, 121.30, 121.33, 121.35, 121.38, 130.8, 130.9, 136.7, 161.9, 163.9; GC-MS calcd for C$_8$H$_6$F$_3$N$_3$ 201. found 201. 2,2-Fifluoro-2-(3-fluorophenyl)ethanamine (4d). To a solution of 15 (2.0 g, 10.0 mmol) in EtOH (30 mL) was added 1 N HCl (15 mL) and Pd(OH)$_2$/C (20%, 200 mg). The reaction mixture was allowed to stir under one atmosphere of H$_2$ for 24 h. The catalyst was removed by filtration and the solvent was evaporated. The resulting yellowish solid was partitioned between diethyl ether (200 mL) and 1 N HCl (200 mL). The aqueous layer was washed with diethyl ether (200 mL) then concentrated to yield amine 4d as a white solid (1.6 g, 91%): $^1$H NMR (500 MHz, D$_2$O) δ 3.60-4.66 (t, J=15.0 Hz, 2H), 7.17-7.30 (m, 3H), 7.40-7.45 (m, 1H); $^{13}$C NMR (125 MHz, D$_2$O) δ 44.6, 44.8, 45.0, 112.6, 112.8, 118.5, 118.7, 121.3, 131.4, 131.5, 161.6, 163.6; LCQ-MS (M+H$^+$) calcd for C$_8$H$_9$F$_3$N 176. found 176; LC-TOF (M+H$^+$) calcd for C$_8$H$_9$F$_3$N 176.06816. found 176.06843.

Example 35

(3S,4S)/(3R,4R)-tert-Butyl-3-((6-(benzyl(tert-butoxycarbonyl)amino)-4-methylpyridin-2-yl)methyl)-4-(2-(tert-butoxycarbonyl(2-(3-fluorophenoxy)ethyl)amino)ethoxy)pyrrolidine-1-carboxylate (17a). To a solution of aldehyde 3 (50 mg, 0.093 mmol) in THF (2 mL) was added 4a (30 mg, 0.186 mmol). The reaction mixture was allowed to stir at room temperature for 10 min before NaHB(OAc)$_3$ (25 mg, 0.116 mmol) was added. The reaction mixture was stirred for an additional 3 h then partitioned between EtOAc (50 mL) and brine (25 mL). The organic layer was dried over Na$_2$SO$_4$ and concentrated to yield crude 16a. To a solution of crude 16a in MeOH (1.5 mL) was added (Boc)$_2$O (30 mg, 0.140 mmol) and Et$_3$N (20 µL, 0.140 mmol). The reaction mixture was stirred at room temperature for 16 h and then partitioned between EtOAc (50 mL) and brine (20 mL). The organic layer was dried over Na$_2$SO$_4$, and the solvents were removed by rotary evaporation. The resulting material was purified by flash column chromatography (EtOAc/hexanes, 1:4-1:2) to yield 17a (35 mg, 60%) as a colorless oil: $^1$H NMR (500 MHz, CDCl$_3$) δ 1.30-1.50 (m, 27H), 2.20-2.40 (m, 3H), 2.45-2.60 (br s, 1H), 2.60-2.80 (m, 1H), 2.80-3.00 (m, 1H), 3.00-3.15 (m, 2H), 3.16-3.80 (m, 10H), 3.90-4.20 (m, 2H), 5.10-5.20 (m, 2H), 6.50-6.80 (m, 3H), 7.10-7.30 (m, 5H), 7.35-7.50 (m, 1H); $^{13}$C NMR (100 MHz, CDCl$_3$) δ 21.4, 28.4, 28.6, 28.7, 34.7, 34.8, 42.3, 42.4, 42.8, 43.0, 47.7, 47.9, 48.1, 48.3, 48.9, 49.0, 49.4, 50.1, 50.4, 50.5, 51.0, 66.7, 67.1, 67.2, 68.2, 68.3, 79.0, 79.3, 79.4, 79.8, 80.1, 80.2, 81.3, 81.4, 102.2, 102.3, 102.4, 102.5, 107.7, 107.9, 110.3, 117.2, 117.3, 120.2, 126.7, 126.8, 127.1, 127.2, 128.3, 130.4, 130.5, 140.0, 148.8, 154.1, 154.5; 154.6, 154.7, 155.5, 157.8, 157.9, 160.2, 162.6, 165.0; LCQ-MS (M+H$^+$) calcd for C$_{43}$H$_{60}$F$_3$N$_4$O$_8$ 779. found 779; LC-TOF (M+H$^+$) calcd for C$_{43}$H$_{60}$F$_3$N$_4$O$_8$ 779.43897. found 779.43823.

Example 36

(3S,4S)/(3R,4R)-tert-Butyl 3-((6-(benzyl(tert-butoxycarbonyl)amino)-4-methylpyridin-2-yl)methyl)-4-(2-(tert-butoxycarbonyl(2-(3-fluorophenyl)cyclopropyl)amino)ethoxy)pyrrolidine-1-carboxylate (17b). 17b was synthesized using a procedure analogous to that for 17a (51%): $^1$H NMR (500 MHz, CDCl$_3$) δ 1.10-1.22 (m, 2H), 1.35-1.50 (m, 28H), 1.65-1.80 (br s, 1H), 2.10-2.20 (br s, 1H), 2.20-2.35 (m, 3H), 2.40-2.80 (m, 3H), 2.80-2.95 (m, 1H), 2.97-3.10 (m, 1H), 3.16-3.21 (m, 1H), 3.22-3.44 (m, 3H), 3.45-3.70 (m, 3H), 4.04-4.10 (m, 1H), 5.10-5.25 (br s, 2H), 6.55-6.65 (m, 1H), 6.65-6.95 (m, 3H), 7.10-7.27 (m, 6H), 6.31-6.45 (m, 1H); $^{13}$C NMR (125 MHz, CDCl$_3$) δ 14.0, 14.4, 14.5, 19.4, 21.3, 21.4, 22.9, 28.4, 28.7, 28.8, 30.0, 30.9, 31.8, 34.8, 34.9, 40.0, 40.1, 42.9, 49.1, 49.5, 50.2, 50.5, 51.1, 60.7, 64.6, 78.2, 79.4, 79.7, 80.2, 81.4, 81.5, 112.9, 113.0, 117.2, 117.3, 120.2, 122.1, 126.8, 127.1, 127.2, 127.3, 128.3, 130.0, 140.1, 148.7, 148.8, 154.1, 154.6, 154.7, 155.0, 157.9, 162.2, 164.1, 171.4, 171.5; LCQ-MS (M+H$^+$) calcd for C$_{44}$H$_{60}$FN$_4$O$_7$ 775. found 775; LC-TOF (M+H$^+$) calcd for C$_{44}$H$_{60}$FN$_4$O$_7$ 775.44405. found 775.44418.

Example 37

(3S,4S)/(3R,4R)-tert-Butyl 3-((6-(benzyl(tert-butoxycarbonyl)amino)-4-methylpyridin-2-yl)methyl)-4-(2-(tert-butoxycarbonyl(2-fluoro-2-(3-fluorophenyepethyl)amino)ethoxy)pyrrolidine-1-carboxylate (17c). 17c was synthesized using a procedure analogous to that for 17a (48%): $^1$H NMR (500 MHz, CDCl$_3$) δ 1.35-1.55 (m, 27H), 2.20-2.35 (m, 3H), 2.50-2.80 (m, 2H), 2.80-2.95 (m, 1H), 3.00-3.22 (m, 2H), 3.23-3.90 (m, 9H), 5.15-5.25 (m, 2H), 5.50-5.80 (m, 1H), 6.50-6.70 (m, 1H), 7.00-7.17 (m, 3H), 7.17-7.27 (m, 6H), 7.30-7.50 (m, 2H); $^{13}$C NMR (125 MHz, CDCl$_3$) δ 14.4, 19.1, 21.3, 21.4, 28.1, 28.3, 28.4, 28.6, 28.7, 28.8, 29.9, 34.7, 42.5, 42.9, 49.1, 49.5, 50.1, 51.1, 54.7, 54.8, 60.6, 68.2, 78.9, 79.4, 79.9, 80.5, 81.4, 81.5, 92.1, 94.1, 112.5, 112.6, 112.7, 112.8, 115.5, 115.6, 115.7, 117.3, 120.2, 121.2, 126.6, 126.7, 126.8, 127.2, 127.3, 127.5, 128.3, 128.7, 130.4, 130.6, 132.6, 140.1, 140.6, 148.8, 154.1, 154.6, 154.7, 155.2, 155.6, 157.8, 162.1, 164.1, 171.4; LCQ-MS (M+H$^+$) calcd for C$_{43}$H$_{59}$F$_2$N$_4$O$_7$ 781. found 781; LC-TOF (M+H$^+$) calcd for C$_{43}$H$_{59}$F$_2$N$_4$O$_7$ 781.43463. found 781.43446.

Example 38

(3S,4S)/(3R,4R)-tert-Butyl 3-((6-(benzyl(tert-butoxycarbonyl)amino)-4-methylpyridin-2-yl)methyl)-4-(2-(tert-butoxycarbonyl(2,2-difluoro-2-(3-fluorophenypethyl)amino)ethoxy)pyrrolidine-1-carboxylate (17d). 17d was synthesized using a procedure analogous to that for 17a (55%): $^1$H NMR (500 MHz, CDCl$_3$) δ 1.35-1.55 (m, 27H), 2.20-2.40 (s, 3H), 2.50-2.80 (m, 2H), 2.80-2.95 (m, 1H), 3.00-3.21 (m, 2H), 3.30-3.79 (m, 6H), 3.80-4.00 (m, 2H), 5.10-5.25 (s, 2H), 6.60-6.70 (br s, 1H), 7.00-7.30 (m, 8H), 7.31-7.60 (m, 2H); $^{13}$C NMR (125 MHz, CDCl$_3$) δ 14.4, 21.2, 21.3, 27.8, 28.1, 28.4, 28.5, 28.7, 29.9, 34.8, 42.3, 42.9, 47.5, 47.7, 49.0, 49.4, 50.1, 50.4, 50.9, 60.6, 67.9, 76.9, 78.9, 79.3, 79.7, 79.8, 80.6, 81.4, 113.0, 113.1, 117.2, 117.5, 120.1, 121.4, 126.7, 126.8, 126.9, 127.0, 127.1, 127.2, 127.5, 127.6, 128.3, 128.5, 128.6, 130.4, 140.0 148.8, 154.1, 154.5, 154.9, 157.8, 161.5, 163.4; LCQ-MS (M+H$^+$) calcd for C$_{43}$H$_{58}$F$_3$N$_4$O$_7$ 799. found 799; LC-TOF (M+H$^+$) calcd for C$_{43}$H$_{58}$F$_3$N$_4$O$_7$ 799.42521. found 799.42577.

Example 39

6-(((3S,4S)/(3R,4R)-4-(2-(2-(3-Fluorophenoxy)ethylamino)ethoxy)pyrrolidin-3-yl)methyl)-4-methylpyridin-2-amine (2a). To a solution of 17a (30 mg, 39 µmol) in EtOH (5.0 mL) was added a 1:1 mixture of EtOH/concentrated HCl (10 mL) and Pd(OH)$_2$/C (20%, 30 mg). The mixture was charged with H$_2$ under the pressure of 500 psi. The reaction mixture was allowed to stir at room temperature for 40 h. The catalyst was removed by filtration through Celite, and the resulting Celite cake was washed with EtOH (4×3 mL) and 2 N HCl (3 mL). The combined filtrates were concentrated to yield inhibitor 2a, a yellow solid, as a hydrochloride salt (15 mg, 85%): $^1$H NMR (500 MHz, D$_2$O) δ 2.08 (s, 3H), 2.60-2.63 (m, 2H), 2.70-2.80 (m, 1H), 2.97-3.03 (m, 1H), 3.13-3.16 (m, 1H), 3.17-3.37 (m, 3H), 3.38-3.50 (m, 3H), 3.54 (br s, 1H), 3.73 (br s, 1H), 4.05 (br s, 1H), 4.17 (br s, 2H), 6.33 (s, 1H), 6.44 (s, 1H), 6.50-6.55 (br s, 1H), 6.58-6.70 (m, 3H), 7.06-7.08 (m, 1H); $^{13}$C NMR (125 MHz, D$_2$O) δ 21.3, 29.4, 41.7, 46.6, 47.0, 47.3, 49.5, 63.0, 64.0, 78.6, 108.4, 108.6, 108.7, 110.4, 110.5, 114.3, 130.9, 131.0, 145.8, 154.0, 158.3, 158.7, 158.8, 162.4, 164.4; LCQ-MS (M+H$^+$) calcd for C$_{21}$H$_{30}$FN$_4$O$_2$ 389. found 389; LC-TOF (M+H$^+$) calcd for C$_{21}$H$_{30}$FN$_4$O$_2$ 389.23473. found 389.23444.

Example 40

6-(((3S,4S)/(3R,4R)-4-(2-(2-(3-Fluorophenyl)cyclopropylamino)ethoxy)pyrrolidin-3-yl)methyl)-4-methylpyridin-2-amine (2b). Inhibitor 2b was synthesized using a procedure analogous to that for 2a (91%): $^1$H NMR (500 MHz, D$_2$O) δ 1.18-1.20 (m, 3H), 2.20 (s, 3H), 2.60-2.72 (m, 2H), 2.75-2.90

(m, 2H), 3.00-3.10 (m, 2H), 3.15-3.33 (m, 3H), 3.34-3.42 (m, 1H), 3.44-3.60 (m, 3H), 3.70-3.80 (m, 1H), 4.09 (s, 1H), 6.46-4.67 (m, 1H), 6.56 (s, 1H), 6.90-7.10 (m, 3H), 7.20-7.25 (m, 1H); $^{13}$C NMR (125 MHz, D$_2$O) δ 15.2, 15.5, 21.3, 29.2, 38.4, 38.5, 41.6, 41.7, 44.2, 44.4, 47.3, 49.5, 55.6, 64.0, 64.4, 78.4, 110.6, 114.3, 114.4, 114.5, 116.2, 116.4, 125.4, 125.6, 130.8, 130.9, 138.3, 145.9, 146.0, 154.1, 158.4, 161.9, 163.9; LCQ-MS (M+H$^+$) calcd for C$_{22}$H$_{30}$FN$_4$O 385. found 385; LC-TOF (M+H$^+$) calcd for C$_{22}$H$_{30}$FN$_4$O 385.24036. found 385.23933.

Example 41

6-(((3S,4S)/(3R,4R)-4-(2-(2-Fluoro-2-(3-fluorophenyl)propylamino)ethoxy)pyrrolidin-3-yl)methyl)-4-methylpyridin-2-amine (2c). Inhibitor 2c was synthesized using a procedure analogous to that for 2a (90%): $^1$H NMR (500 MHz, D$_2$O) δ 2.14 (s, 3H), 2.61-2.77 (m, 2H), 2.78-2.95 (m, 2H), 2.96-3.10 (m, 1H), 3.11-3.25 (m, 2H), 3.26-3.40 (m, 2H), 3.41-4.60 (m, 3H), 3.63-3.80 (m, 1H), 4.00-4.15 (m, 1H), 5.78-5.80 (d, J=9.0 Hz, 0.5H), 5.81-5.90 (d, J=9.0 Hz, 0.5H), 6.41-6.43 (d, J=7.5 Hz, 1H), 6.50-6.55 (d, J=8.0 Hz, 1H), 6.80-6.95 (m, 1H), 6.96-7.15 (m, 2H), 7.16-7.40 (m, 1H); $^{13}$C NMR (125 MHz, D$_2$O) δ 21.29, 21.34, 29.23, 29.28, 29.32, 29.8, 31.4, 41.6, 41.7, 47.1, 47.3, 47.6, 48.4, 49.5, 51.6, 52.1, 63.9, 64.0, 64.2, 78.4, 88.6, 89.9, 110.6, 112.8, 113.0, 114.2, 114.3, 114.4, 114.8, 115.6, 115.8, 116.7, 116.8, 121.8, 124.9, 126.9, 127.4, 128.9, 129.1, 130.8, 130.9, 131.1, 131.2, 137.1, 138.9, 139.0, 145.8, 145.9, 154.0, 158.4, 161.8, 161.9, 163.7, 163.8; LCQ-MS (M+H$^+$) calcd for C$_{21}$H$_{29}$F$_2$N$_4$O 391. found 391; LC-TOF (M+H$^+$) calcd for C$_{21}$H$_{29}$F$_2$N$_4$O 391.23094. found 391.23012.

Example 42

6-(((3S,4S)/(3R,4R)-4-(2-(2,2-Difluoro-2-(3-fluorophenyl)ethylamino)ethoxy)pyrrolidin-3-yemethyl)-4-methylpyridin-2-amine (2d). Inhibitor 2d was synthesized using a procedure analogous to that for 2a (91%): $^1$H NMR (500 MHz, D$_2$O) δ 2.19 (s, 3H), 2.68-2.70 (m, 2H), 2.80-2.92 (m, 1H), 2.93-3.10 (m, 1H), 3.20-3.30 (d, J=13.0 Hz, 1H), 3.38 (s, 3H), 3.50-3.60 (d, J=14.0 Hz, 1H), 3.65 (br s, 1H), 3.70-3.90 (m, 3H), 4.15 (s, 1H), 6.45 (s, 1H), 6.55 (s, 1H), 7.10-7.35 (m, 3H), 7.42 (br s, 1H); $^{13}$C NMR (125 MHz, D$_2$O) δ 21.3, 29.3, 41.5, 47.3, 47.7, 47.8, 49.4, 51.9, 63.8, 78.5, 110.6, 112.5, 114.2, 118.6, 118.8, 121.2, 131.5, 145.8, 154.1, 158.4, 161.6; LCQ-MS (M+H$^+$) calcd for C$_{21}$H$_{28}$F$_3$N$_4$O 409. found 409; LC-TOF (M+H$^+$) calcd for C$_{21}$H$_{28}$F$_3$N$_4$O 409.22152. found 409.22076.

Examples 43-57 can be considered in the context of Schemes 5-8, above.

Example 43

General Method (A) for Reductive Amination. To a solution of aldehyde 8a or 8b (0.1 mmol) in THF (3 mL) was added ethanamine (0.2 mmol), followed by NaHB(OAc)$_3$ (0.12 mmol). The mixture was stirred at room temperature for an additional 3 h, and then concentrated. The crude product was purified by flash column chromatography (EtOAc/hexanes, 2:1-4:1) to yield the corresponding secondary amines as colorless oils which were used without further purification.

Example 44

General Method (B) for Boc-protection. To a solution of secondary amine (0.5 mmol) in MeOH (10 mL) was added (Boc)$_2$O (164 mg, 0.75 mmol) and TEA (140 μL, 1.0 mmol). The reaction mixture was allowed to stir at room temperature for 30 min. The solvent was removed by rotary evaporation, and the resulting material was purified by flash column chromatography (EtOAc/hexanes, 1:4-1:2) to yield 9a-f as a colorless oil.

Example 45

General Method (C) for Catalytic hydrogenation. To a solution of 9a-f (0.2 mmol) in EtOH (20 mL) was added Pd(OH)$_2$/C (100 mg). The reaction vessel was charged with H$_2$, heated at 60° C. for 24-48 h, then cooled to room temperature. The catalyst was removed by filtration, and the resulting solution was concentrated by rotary evaporation. The crude material was purified by flash column chromatography (EtOAc/hexanes, 1:4 1:2) to yield 10a-f as a white foamy solid.

Example 46

General Method (D) for Boc-deprotection. To a solution of 10a-f (50 μmol) in MeOH (0.5 mL) was added 6 N HCl (1.0 mL). The reaction mixture was allowed to sit at room temperature for 12 h. The solvent was removed by rotary evaporation. The crude product was recrystallized using cold diethyl ether to provide 2da-2dd and 2e-2f as pale yellow solids.

Example 47

9a was synthesized by general methods A and B using aldehyde 8b as a starting material (55%): $^1$H NMR (500 MHz, CDCl$_3$) δ 1.35-1.55 (m, 27H), 2.20-2.40 (s, 3H), 2.50-2.80 (m, 2H), 2.80-2.95 (m, 1H), 3.00-3.21 (m, 2H), 3.30-3.79 (m, 6H), 3.80 4.00 (m, 2H), 5.10-5.25 (s, 2H), 6.60-6.70 (br s, 1H), 7.00-7.30 (m, 8H), 7.31 7.60 (m, 2H); $^{13}$C NMR (125 MHz, CDCl$_3$) δ 14.4, 21.2, 21.3, 27.8, 28.1, 28.4, 28.5, 28.7, 29.9, 34.8, 42.3, 42.9, 47.5, 47.7, 49.0, 49.4, 50.1, 50.4, 50.9, 60.6, 67.9, 76.9, 78.9, 79.3, 79.7, 79.8, 80.6, 81.4, 113.0, 113.1, 117.2, 117.5, 120.1, 121.4, 126.7, 126.8, 126.9, 127.0, 127.1, 127.2, 127.5, 127.6, 128.3, 128.5, 128.6, 130.4, 140.0 148.8, 154.1, 154.5, 154.9, 157.8, 161.5, 163.4; LCQ-MS (M+H$^+$) calcd for C$_{43}$H$_{58}$F$_3$N$_4$O$_7$ 799. found 799; LC-TOF (M+H$^+$) calcd for C$_{43}$H$_{58}$F$_3$N$_4$O$_7$ 799.4252. found 799.4258.

Example 48

9b was synthesized by general methods A and B using aldehyde 8a as a starting material (55%): $^1$H NMR (500 MHz, CDCl$_3$) δ 1.35-1.55 (m, 27H), 2.20-2.40 (s, 3H), 2.50-2.80 (m, 2H), 2.80-2.95 (m, 1H), 3.00-3.21 (m, 2H), 3.30-3.79 (m, 6H), 3.80 4.00 (m, 2H), 5.10-5.25 (s, 2H), 6.60-6.70 (br s, 1H), 7.00-7.30 (m, 8H), 7.31-7.60 (m, 2H); $^{13}$C NMR (125 MHz, CDCl$_3$) δ 14.4, 21.2, 21.3, 27.8, 28.1, 28.4, 28.5, 28.7, 29.9, 34.8, 42.3, 42.9, 47.5, 47.7, 49.0, 49.4, 50.1, 50.4, 50.9, 60.6, 67.9, 76.9, 78.9, 79.3, 79.7, 79.8, 80.6, 81.4, 113.0, 113.1, 117.2, 117.5, 120.1, 121.4, 126.7, 126.8, 126.9, 127.0, 127.1, 127.2, 127.5, 127.6, 128.3, 128.5, 128.6, 130.4, 140.0 148.8, 154.1, 154.5, 154.9, 157.8, 161.5, 163.4; LCQ-MS (M+H$^+$) calcd for C$_{43}$H$_{58}$F$_3$N$_4$O$_7$ 799. found 799; LC-TOF (M+H$^+$) calcd for C$_{43}$H$_{58}$F$_3$N$_4$O$_7$ 799.4252. found 799.4248

Example 49

9c was synthesized by general methods A and B using aldehyde 8a as a starting material (55%): $^1$H NMR (500 MHz, CDCl₃) δ 1.20-1.50 (m, 27H), 2.25 2.35 (m, 3H), 2.45-2.65 (m, 1H), 2.66-2.70 (m, 1H), 2.80-2.95 (m, 1H), 3.00-3.10 (m, 1H), 3.10-3.20 (m, 1H), 3.25-3.70 (m, 7H), 3.80-4.00 (m, 2H), 5.10-5.20 (m, 2H), 6.60 6.70 (m, 1H), 7.00-7.15 (m, 2H), 7.16-7.20 (m, 1H), 7.21-7.27 (m, 4H), 7.35-7.60 (m, 3H); $^{13}$C NMR (125 MHz, CDCl₃) δ 13.7, 14.2, 19.1, 21.0, 21.1, 24.7, 27.91, 27.96, 28.01, 28.2, 28.3, 28.5, 30.6, 34.4, 34.5, 34.6, 42.0, 42.1, 42.6, 42.7, 47.4, 47.5, 47.6, 47.8, 48.8, 49.3, 49.9, 50.1, 50.3, 50.8, 53.4, 53.8, 54.0, 60.4, 64.4, 67.7, 67.8, 68.0, 78.7, 78.8, 79.1, 79.2, 79.3, 79.6, 80.3, 81.17, 81.22, 115.2, 115.4, 115.6, 115.7, 117.0, 117.1, 119.9, 126.5, 126.6, 126.9, 127.0, 127.5, 128.1, 131.5, 139.7, 139.8, 148.6, 153.9, 154.3, 154.4, 154.5, 154.6, 154.7, 154.8, 155.1, 157.4, 157.5, 157.6, 162.7, 164.6, 171.2; LC-TOF (M+H⁺) calcd for $C_{43}H_{58}F_3N_4O_7$ 799.4258. found 799.4237.

Example 50

9d was synthesized by general methods A and B using aldehyde 8a as a starting material (55%): $^1$H NMR (500 MHz, CDCl₃) δ 1.20-1.50 (m, 27H), 2.25 2.35 (m, 3H), 2.45-2.65 (m, 1H), 2.66-2.71 (m, 1H), 2.80-2.95 (m, 1H), 3.00-3.10 (m, 1H), 3.10-3.20 (m, 1H), 3.25-3.70 (m, 7H), 3.80-4.00 (m, 2H), 5.10-5.20 (m, 2H), 6.60 6.70 (m, 1H), 7.00-7.60 (m, 12H); $^{13}$C NMR (125 MHz, CDCl₃) δ 13.7, 14.2, 19.1, 21.0, 21.1, 24.7, 27.91, 27.96, 28.01, 28.2, 28.3, 28.5, 30.6, 34.4, 34.5, 34.6, 42.0, 42.1, 42.6, 42.7, 47.4, 47.5, 47.6, 47.8, 48.8, 49.3, 49.9, 50.1, 50.3, 50.8, 53.4, 53.8, 54.0, 60.4, 64.4, 67.7, 67.8, 68.0, 78.7, 78.8, 79.1, 79.2, 79.3, 79.6, 80.3, 81.17, 81.22, 115.2, 115.4, 115.6, 115.7, 117.0, 117.1, 119.9, 126.5, 126.6, 126.9, 127.0, 127.5, 128.1, 131.5, 139.7, 139.8, 148.6, 153.9, 154.3, 154.4, 154.5, 154.6, 154.7, 154.8, 155.1, 157.4, 157.5, 157.6, 162.7, 164.6, 171.2; LC-TOF (M+H⁺) calcd for $C_{43}H_{59}F_2N_4O_7$ 781.4352. found 781.4366.

Example 51

9f was synthesized by general methods A and B using aldehyde 8b as a starting material (55%): $^1$H NMR (500 MHz, CDCl₃) δ 1.40-1.55 (m, 27H), 2.27 2.29 (m, 3H), 2.45-2.67 (m, 1H), 2.68-2.75 (m, 1H), 2.85-2.95 (m, 1H), 3.00-3.11 (m, 1H), 3.12-3.20 (m, 1H), 3.30-3.45 (m, 3H), 3.46-3.65 (m, 3H), 4.05-4.20 (m, 2H), 5.16 (s, 2H), 6.67 (s, 1H), 7.17-7.20 (m, 1H), 7.21-7.26 (m, 4H), 7.30-7.45 (m, 2H), 7.50 7.70 (m, 1H), 7.75-7.85 (m, 1H), 8.60-8.71 (m, 1H); $^{13}$C NMR (125 MHz, CDCl₃) δ 14.2, 21.11, 21.13, 24.7, 28.0, 28.1, 28.2, 28.3, 28.5, 29.7, 34.4, 34.5, 36.6, 42.2, 42.6, 42.7, 47.6, 47.7, 48.0, 48.8, 49.2, 49.89, 49.92, 50.1, 50.2, 50.8, 60.4, 67.5, 67.6, 67.7, 78.7, 79.1, 79.6, 80.2, 81.1, 81.2, 117.0, 117.1, 120.0, 120.4, 120.5, 124.76, 124.84, 126.4, 126.5, 126.6, 126.9, 127.0, 128.06, 128.11, 136.9, 137.0, 139.8, 139.9, 148.5, 149.3, 149.5, 153.8, 154.3, 154.4, 154.5, 154.7, 155.0, 155.4, 157.7; LC-TOF (M+H⁺) calcd for $C_{42}H_{58}F_2N_5O_7$ 782.4304. found 782.4299.

Example 52

Inhibitor compound 2da was synthesized by general methods C and D using 9a as a starting material (55%): $^1$H NMR (500 MHz, D₂O) δ 2.29 (s, 3H), 2.78-2.81 (m, 2H), 2.95 3.05 (dd, J=8.0, 15.0 Hz, 1H), 3.15-3.20 (t, J=6.0, 1H), 3.31-3.35 (dd, J=3.0, 13.0 Hz, 1H), 3.40-3.55 (m, 3H), 3.63-3.66 (d, J=13.0 Hz, 1H), 3.71-3.79 (m, 1H), 3.87-3.95 (m, 3H), 4.24-4.26 (t, J=3.0 Hz, 1H), 6.55 (s, 1H), 6.64 (s, 1H), 7.25-7.29 (dt, J=2.5, 8.5 Hz, 1H), 7.34-7.36 (dd, J=2.5, 14.0 Hz, 1H), 7.38-7.40 (dd, J=2.5, 8.0 Hz, 1H), 7.49 7.52 (dd, J=6.0, 8.0 Hz, 1H); $^{13}$C NMR (125 MHz, D₂O) δ 21.0, 29.1, 41.3, 47.0, 47.5, 49.2, 51.5, 51.7, 51.9, 63.6, 78.3, 110.4, 112.3, 112.5, 114.0, 118.2, 118.4, 118.6, 121.0, 131.2, 131.3, 134.2, 145.5, 153.9, 158.1, 161.4, 163.3; LC-TOF (M+H⁺) calcd for $C_{21}H_{28}F_3N_4O$ 409.2215. found 409.2226.

Example 53

Inhibitor compound 2db was synthesized by general methods C and D using 9b as a starting material (55%): $^1$H NMR (500 MHz, D₂O) δ 2.29 (s, 3H), 2.78-2.81 (m, 2H), 2.95 3.05 (dd, J=8.0, 15.0 Hz, 1H), 3.15-3.20 (t, J=6.0, 1H), 3.31-3.35 (dd, J=3.0, 13.0 Hz, 1H), 3.40-3.55 (m, 3H), 3.63-3.66 (d, J=13.0 Hz, 1H), 3.71-3.79 (m, 1H), 3.87-3.95 (m, 3H), 4.24-4.26 (t, J=3.0 Hz, 1H), 6.55 (s, 1H), 6.64 (s, 1H), 7.25-7.29 (dt, J=2.5, 8.5 Hz, 1H), 7.34-7.36 (dd, J=2.5, 14.0 Hz, 1H), 7.38-7.40 (dd, J=2.5, 8.0 Hz, 1H), 7.49 7.52 (dd, J=6.0, 8.0 Hz, 1H); $^{13}$C NMR (125 MHz, D₂O) δ 21.0, 29.1, 41.3, 47.0, 47.5, 49.2, 51.5, 51.7, 51.9, 63.6, 78.3, 110.4, 112.3, 112.5, 114.0, 118.2, 118.4, 118.6, 121.0, 131.2, 131.3, 134.2, 145.5, 153.9, 158.1, 161.4, 163.3; LC-TOF (M+H⁺) calcd for $C_{21}H_{28}F_3N_4O$ 409.2215. found 409.2223.

Example 54

Inhibitor compound 2dc was synthesized by general methods C and D using 9c as a starting material (55%): $^1$H NMR (500 MHz, D₂O) δ 2.30 (s, 3H), 2.78-2.81 (m, 2H), 2.95 3.05 (dd, J=8.0, 15.0 Hz, 1H), 3.15-3.20 (t, J=6.0, 1H), 3.31-3.35 (dd, J=3.0, 13.0 Hz, 1H), 3.40-3.55 (m, 3H), 3.63-3.66 (d, J=13.0 Hz, 1H), 3.71-3.79 (m, 1H), 3.87-3.95 (m, 3H), 4.24-4.26 (t, J=3.0 Hz, 1H), 6.55 (s, 1H), 6.64 (s, 1H), 7.21-7.25 (dd, J=8.5, 8.5 Hz, 2H), 7.59-7.62 (dd, J=5.0, 8.5 Hz, 2H); $^{13}$C NMR (125 MHz, D₂O) δ 21.0, 29.0, 41.3, 47.0, 47.4, 49.2, 51.7, 51.9, 51.9, 63.6, 78.3, 110.4, 113.9, 116.0, 116.1, 118.7, 127.42, 127.47, 127.55, 127.59, 145.5, 153.9, 158.1; LC-TOF (M+H⁺) calcd for $C_{21}H_{28}F_3N_4O$ 409.2215. found 409.2230.

Example 55

Inhibitor compound 2dd was synthesized by general methods C and D using 9d as a starting material (55%): $^1$H NMR (500 MHz, D₂O) δ 2.30 (s, 3H), 2.73-2.84 (m, 2H), 2.95 3.05 (dd, J=8.5, 15.0 Hz, 1H), 3.10-3.20 (t, J=6.0, 1H), 3.31-3.35 (dd, J=3.0, 13.5 Hz, 1H), 3.40-3.55 (m, 3H), 3.63-3.66 (d, J=13.5 Hz, 1H), 3.71-3.79 (m, 1H), 3.87-3.95 (m, 3H), 4.24-4.26 (t, J=3.0 Hz, 1H), 6.55 (s, 1H), 6.64 (s, 1H), 7.45-7.65 (m, 5H); $^{13}$C NMR (125 MHz, D₂O) δ 21.0, 29.0, 41.3, 47.0, 47.4, 49.2, 51.6, 51.8, 52.0, 63.6, 78.2, 110.4, 113.9, 119.0, 120.9, 124.81, 124.86, 124.91, 129.1, 131.6, 131.9, 132.1, 145.5, 153.9, 158.1; LC-TOF (M+H⁺) calcd for $C_{21}H_{29}F_2N_4O$ 391.2309. found 391.2337.

Example 56

Inhibitor compound 2e was synthesized by general methods C and D using 9e as a starting material (55%): $^1$H NMR (500 MHz, D₂O) δ 0.85-0.95 (d, J=2.5, 3H), 1.45 1.55 (m, 1H), 1.61-1.70 (m, 1H), 1.71-1.97 (m, 3H), 2.00-2.10 (m, 1H), 2.35-2.45 (m, 1H), 2.46 2.57 (m, 1H), 2.90-3.00 (t, J=6.0, 1H), 3.16-3.21 (m, 1H), 3.30-3.50 (m, 4H), 3.51 3.60 (d, J=13.5 Hz, 1H), 3.61-3.70 (m, 1H), 3.75-3.90 (m, 3H), 4.14s-4.16 (t, J=3.0 Hz, 1H), 7.45-7.65 (m, 5H); $^{13}$C NMR (125 MHz, D₂O) δ 17.5, 17.6, 18.2, 26.8, 27.2, 27.3, 32.6, 32.9, 40.0, 40.2, 48.3, 48.9, 49.1, 49.6, 50.6, 52.2, 58.8, 65.2, 79.9, 80.0, 115.4, 115.6, 116.8, 117.0, 126.0, 132.1, 132.2, 140.2, 163.1, 165.0, 168.4; LC TOF (M+H$^+$) calcd for C$_{21}$H$_{33}$F$_2$N$_4$O 395.2622. found 395.2633.

Example 57

Inhibitor compound 2f was synthesized by general methods C and D using 9f as a starting material (55%): $^1$H NMR (500 MHz, D$_2$O) δ 1.40-1.50 (m, 1H), 1.51-1.60 (m, 2H), 1.79 1.90 (m, 2H), 1.91-1.98 (d, J=13.5 Hz, 1H), 2.20 (s, 3H), 2.65-2.75 (m, 1H), 2.79 2.85 (m, 1H), 2.94-2.96 (d, J=7.5 Hz, 1H), 2.97-3.00 (m, 1H), 3.07-3.12 (dd, J=11.5, 11.5 Hz, 1H), 3.20-3.26 (dd, J=0.5, 13.0 Hz, 1H), 3.31-3.47 (m, 4H), 3.52-3.55 (d, J=13.5 Hz, 1H), 3.61-3.64 (m, 1H), 3.74-3.82 (m, 5H), 4.11 (s, 1H), 6.52 (s, 1H), 6.57 (s, 1H); $^{13}$C NMR (125 MHz, D$_2$O) δ 20.4, 21.05, 21.06, 22.4, 28.95, 29.01, 41.48, 41.51, 45.1, 47.0, 48.08, 48.14, 49.4, 57.7, 63.7, 63.9, 78.3, 78.4, 110.4, 114.09, 114.12, 145.7, 153.9, 158.1; LC-TOF (M+H$^+$) calcd for C$_{20}$H$_{34}$F$_2$N$_5$O 398.2742. found 398.2726.

Enzyme Assays

Example 58

IC$_{50}$ values for inhibitors 2a-d were measured for the three different isoforms of NOS including rat nNOS, bovine eNOS, and murine macrophage iNOS using L-arginine as a substrate. The three isozymes were recombinant enzymes, which were overexpressed (in *E. coli*) and isolated as reported. The formation of nitric oxide was measured using a hemoglobin capture assay described previously. (Hevel, supra.) All NOS isozymes were assayed at room temperature in a 100 mM Hepes buffer (pH 7.4) containing 10 µM L-arginine, 1.6 mM CaCl$_2$, 11.6 µg/mL calmodulin, 100 µM DTT, 100 µM NADPH, 6.5 µM H$_4$B, 3.0 mM oxyhemoglobin (for iNOS assays, no Ca$^{2+}$ and calmodulin was added). The assay was initiated by the addition of enzyme, and the initial rates of the enzymatic reactions were determined by monitoring the formation of NO-hemoglobin complex at 401 nm from 0 to 60 s after. The corresponding K$_i$ values of inhibitors were calculated from the IC$_{50}$ values using equation 1 with known K$_m$ values (rat nNOS, 1.3 µM; iNOS, 8.3 µM; eNOS, 1.7 µM).

$$K_i = IC_{50}/(1+[S]/K_m) \quad (1)$$

Example 59

IC$_{50}$ values for inhibitors 2da-2dd and 2e-f were measured for the three different isoforms of NOS including rat nNOS, bovine eNOS, and murine macrophage iNOS using L-arginine as a substrate. The three isozymes were recombinant enzymes, which were overexpressed (in *E. coli*) and isolated as reported. The formation of nitric oxide was measured using a hemoglobin capture assay described previously. All NOS isozymes were assayed at room temperature in a 100 mM Hepes buffer (pH 7.4) containing 10 µM L-arginine, 1.6 mM CaCl$_2$, 11.6 µg/mL calmodulin, 100 µM DTT, 100 µM NADPH, 6.5 µM H$_4$B, 3.0 µM oxyhemoglobin (for iNOS assays, no Ca$^{2+}$ and calmodulin was added). The assay was initiated by the addition of enzyme, and the initial rates of the enzymatic reactions were determined by monitoring the formation of NO-hemoglobin complex at 401 nm for 60 s. The corresponding K$_i$ values of inhibitors were calculated from the IC$_{50}$ values using equation 1 with known K$_m$ values, as above.

Inhibitor Complex Crystal Preparation

Example 60

The nNOS or eNOS heme domain protein used for crystallographic studies were produced by limited trypsin digest from the corresponding full length enzymes and further purified through a Superdex 200 gel filtration column (GE Healthcare) as described previously. (See, Li, H.; Shimizu, H.; Flinspach, M.; Jamal, J.; Yang, W.; Xian, M.; Cai, T.; Wen, E. Z.; Jia, Q.; Wang, P. G.; Poulos, T. L., The novel binding mode of N-alkyl-N'-hydroxyguanidine to neuronal nitric oxide synthase provides mechanistic insights into NO biosynthesis. *Biochemistry* 2002, 41, 13868-13875; and Flinspach, M. L.; Li, H.; Jamal, J.; Yang, W.; Huang, H.; Hah, J. M.; Gomez Vidal, J. A.; Litzinger, E. A.; Silverman, R. B.; Poulos, T. L., Structural basis for dipeptide amide isoform-selective inhibition of neuronal nitric oxide synthase. *Nat Struct Mol Biol* 2004, 11, 54-59.) The enzyme-inhibitor complex crystals were obtained by soaking rather than co-crystallization, as reported. The nNOS heme domain at 7-9 mg/mL containing 20 mM histidine or the eNOS heme domain at 20 mg/mL with 2 mM imidazole were used for the sitting drop vapor diffusion crystallization setup under the conditions previously reported. Fresh crystals (1-2 day old) were first passed stepwise through cryo-protectant solutions described and then soaked with 10 mM inhibitor for 4-6 h at 4° C. before being mount on nylon loops and flash cooled by plunging into liquid nitrogen. (See, Li, H.; Shimizu, H.; Flinspach, M.; Jamal, J.; Yang, W.; Xian, M.; Cai, T.; Wen, E. Z.; Jia, Q.; Wang, P. G.; Poulos, T. L., The novel binding mode of N-alkyl-N'-hydroxyguanidine to neuronal nitric oxide synthase provides mechanistic insights into NO biosynthesis. *Biochemistry* 2002, 41, 13868-13875; Flinspach, M. L.; Li, H.; Jamal, J.; Yang, W.; Huang, H.; Hah, J. M.; Gomez-Vidal, J. A.; Litzinger, E. A.; Silverman, R. B.; Poulos, T. L., Structural basis for dipeptide amide isoform-selective inhibition of neuronal nitric oxide synthase. *Nat Struct Mol Biol* 2004, 11, 54-59.) Crystals were stored in liquid nitrogen until data collection.

X-ray Diffraction Data Collection, Processing, and Structure Refinement

Example 61

The cryogenic (100K) x-ray diffraction data were collected remotely at various beamlines at Stanford Synchrotron Radiation Lightsource through the data collection control software Blu-Ice and the crystal mounting robot. (McPhillips, T. M.; McPhillips, S. E.; Chiu, H. J.; Cohen, A. E.; Deacon, A. M.; Ellis, P. J.; Garman, E.; Gonzalez, A.; Sauter, N. K.; Phizackerley, R. P.; Soltis, S. M.; Kuhn, P., Blu-Ice and the Distributed Control System: software for data acquisition and instrument control at macromolecular crystallography beamlines. *J Synchrotron Radiat* 2002, 9, 401-406.) Raw data frames were indexed, integrated, and scaled using HKL2000. (6) Typically, each data set consisted of 90 to 100 degree of data with 0.5 degree frame width for both nNOS and eNOS crystals because of their identical orthorhombic P2$_1$2$_1$2$_1$ space group symmetry.

The binding of inhibitors was detected by the initial difference Fourier maps calculated with REFMAC. (Murshudov, G. N.; Vagin, A. A.; Dodson, E. J., Refinement of Macromolecular Structures by the Maximum-Likelihood Method. *Acta Cryst.* 1997, D53, 240 255.) The inhibitor molecules were then modeled in O (Jones, T. A.; Zou, J.-Y.; Cowan, S. W.; Kjeldgaarrd, M., Improved methods for building models in electron density and the location of errors in these models. *Acta Cryst.* 1991, A47, 110-119) or COOT (Emsley, P.; Cowtan, K., Coot: model-building tools for molecular graphics. *Acta Cryst.* 2004, D60, 2126-2132) and refined using REFMAC. Water molecules were added in REFMAC and checked by COOT. The TLS protocol was implemented in the final stage of refinements with each subunit as one TLS group. (Winn, M. D.; Isupov, M. N.; Murshudov, G. N., Use of TLS parameters to model anisotropic displacements in macromolecular refinement. *Acta Cryst.* 2001, D57, 122-133.) The refined structures were validated in COOT before deposition to RCSB protein data bank. The crystallographic data collection and structure refinement statistics are summarized in Table 5 with PDB accession codes included.

TABLE 5

Crystallographic data collection and refinement statistics

| Data set[1] | nNOS-2da | nNOS-2db | nNOS-2dc | nNOS-2dd |
|---|---|---|---|---|
| Data collection PDB code | | | | |
| Space group | $P2_12_12_1$ | $P2_12_12_1$ | $P2_12_12_1$ | $P2_12_12_1$ |
| Cell dimensions | | | | |
| a, b, c (Å) | 52.3, 111.7, 164.4 | 52.3, 111.5, 164.4 | 51.8, 111.2, 164.1 | 51.9, 110.4, 164.0 |
| Resolution (Å) | 2.10 (2.14-2.10) | 1.87 (1.90-1.87) | 2.00 (2.03-2.00) | 1.92 (1.95-1.92) |
| $R_{sym}$ or $R_{merge}$ | 0.080 (0.59) | 0.053 (0.36) | 0.078 (0.40) | 0.050 (0.32) |
| $I/\sigma I$ | 9.1 (2.2) | 13.5 (3.9) | 7.6 (1.8) | 11.5 (2.6) |
| No. unique reflections | 56,857 | 79,054 | 63,439 | 73,017 |
| Completeness (%) | 99.4 (99.5) | 98.2 (96.5) | 96.7 (80.9) | 99.4 (89.8) |
| Redundancy | 5.6 (2.9) | 4.1 (4.1) | 3.9 (3.1) | 4.1 (3.6) |
| Refinement | | | | |
| Resolution (Å) | 2.10 | 1.87 | 2.00 | 1.92 |
| No. reflections used | 54,011 | 75,069 | 60,245 | 69,320 |
| $R_{work}/R_{free}$ | 0.175/0.211 | 0.178/0.209 | 0.201/0.249 | 0.173/0.210 |
| No. atoms | | | | |
| Protein | 6,671 | 6,689 | 6,676 | 6,707 |
| Ligand/ion | 187 | 223 | 190 | 217 |
| Water | 434 | 479 | 190 | 417 |
| R.m.s. deviations | | | | |
| Bond lengths (Å) | 0.013 | 0.012 | 0.015 | 0.013 |
| Bond angles (°) | 1.325 | 1.390 | 1.554 | 1.456 |

| | nNOS-2e | nNOS-2f | eNOS-2db | eNOS-2f |
|---|---|---|---|---|
| Data collection PDB code | | | | |
| Space group | $P2_12_12_1$ | $P2_12_12_1$ | $P2_12_12_1$ | $P2_12_12_1$ |
| Cell dimensions | | | | |
| a, b, c (Å) | 52.1, 110.9, 164.2 | 52.2, 111.4, 164.7 | 58.0, 107.0, 156.9 | 57.9, 106.9, 157.0 |
| Resolution (Å) | 1.81 (1.84-1.81) | 2.10 (2.14-2.10) | 2.65 (2.70-2.65) | 2.75 (2.80-2.75) |
| $R_{sym}$ or $R_{merge}$ | 0.048 (0.38) | 0.069 (0.55) | 0.121 (0.58) | 0.103 (0.65) |
| $I/\sigma I$ | 12.1 (2.7) | 9.2 (2.4) | 9.7 (1.9) | 12.4 (1.9) |
| No. unique reflections | 86,908 | 56,364 | 28,366 | 25,670 |
| Completeness (%) | 99.0 (92.5) | 99.2 (100.0) | 97.3 (99.1) | 95.6 (94.4) |
| Redundancy | 4.0 (3.8) | 4.1 (4.1) | 3.7 (3.7) | 3.9 (4.0) |
| Refinement | | | | |
| Resolution (Å) | 1.81 | 2.10 | 2.65 | 2.74 |
| No. reflections used | 82,532 | 53,523 | 26,957 | 24,379 |
| $R_{work}/R_{free}$[2] | 0.178/0.209 | 0.171/0.207 | 0.185/0.254 | 0.186/0.262 |
| No. atoms | | | | |
| Protein | 6,716 | 6,676 | 6,451 | 6,419 |
| Ligand/ion | 217 | 185 | 197 | 195 |
| Water | 459 | 319 | 111 | 60 |
| R.m.s. deviations | | | | |
| Bond lengths (Å) | 0.013 | 0.013 | 0.014 | 0.014 |
| Bond angles (°) | 1.360 | 1.347 | 1.502 | 1.519 |

[1] See Schemes 6-8 for nomenclature and chemical formula of inhibitors.

[2] $R_{free}$ was calculated with the 5% of reflections set aside throughout the refinement. For each NOS isoform the set of reflections for the $R_{free}$ calculation were kept the same for all data sets according to those used in the data of the starting model.

As demonstrated by the foregoing, this invention provides a new series of selective nNOS inhibitors. Without limitation, biological evaluation of these new inhibitors led to the discovery of several inhibitors, which not only retain most of the activity of compound 1, but also have improved membrane permeability.

We claim:

1. A nitric oxide synthase inhibitor compound of a formula

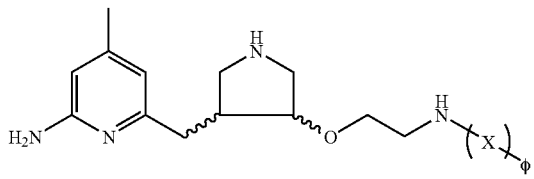

wherein X is selected from divalent ethylene oxide, cyclopropyl, monofluoroethylene and difluoroethylene moieties; and Φ is selected from phenyl, substituted phenyl, piperidinyl and substituted piperidinyl moieties, or a salt thereof.

2. The compound of claim 1 wherein X is selected from cyclopropyl and difluoroethylene moieties.

3. The compound of claim 2 wherein Φ is selected from phenyl and substituted phenyl moieties.

4. The compound of claim 3 wherein said substituent is selected from halide and alkyl substituents.

5. The compound of claim 4 wherein Φ is m-fluorophenyl.

6. The compound of claim 1 selected from the (S,S) and (R,R) enantiomers.

7. The compound of claim 1 wherein said compound is an ammonium salt.

8. The compound of claim 7 wherein said ammonium salt has a counter ion that is a conjugate base of a protic acid.

9. The compound of claim 1 complexed with a nitric oxide synthase enzyme.

10. A nitric oxide synthase inhibitor compound of a formula

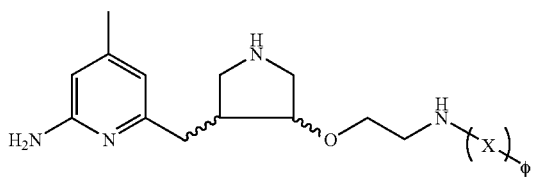

wherein X is selected from divalent ethylene oxide, cyclopropyl, monofluoroethylene and difluoroethylene moieties; and Φ is selected from phenyl, substituted phenyl, piperidinyl and substituted piperidinyl moieties, or a salt thereof wherein the pyridine of said compound is at least partially reduced.

11. The compound of claim 10 complexed with a nitric oxide synthase enzyme.

12. A nitric oxide synthase inhibitor compound of a formula

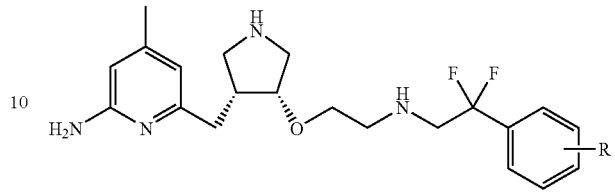

wherein R is selected from H, halide and alkyl moieties; or a salt thereof.

13. The compound of claim 12 wherein R is halide.

14. The compound of claim 13 wherein R is meta-substituted fluoride.

15. The compound of claim 12 wherein said compound is an ammonium salt.

16. The compound of claim 15 wherein said ammonium salt has a counter ion that is a conjugate base of a protic acid.

17. A method inhibiting a nitric oxide synthase comprising contacting a nitric oxide synthase with an effective amount of a compound of a formula

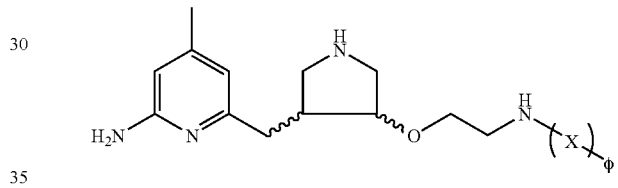

wherein X is selected from divalent ethylene oxide, cyclopropyl, monofluoroethylene and difluoroethylene moieties; and Φ is selected from phenyl, substituted phenyl, piperidinyl and substituted piperidinyl moieties, or a salt thereof.

18. The method of claim 17 wherein X is selected from cyclopropyl and difluoroethylene moieties.

19. The method of claim 18 wherein Φ is selected from phenyl and substituted phenyl moieties.

20. The method of claim 19 wherein Φ is m-fluorophenyl.

21. The method of claim 17 wherein X is a difluoroethylene moiety and said compound is selected from the (S,S) and (R,R) enantiomers.

22. The method of claim 21 wherein said compound is the (R,R) enantiomer, and said method selective for inhibition of neuronal nitric oxide synthase.

* * * * *